(12) United States Patent
Ochiai et al.

(10) Patent No.: US 10,323,250 B2
(45) Date of Patent: Jun. 18, 2019

(54) **PROMOTER EXHIBITING HIGH EXPRESSION ACTIVITY IN *MORTIERELLA* MICROORGANISMS**

(71) Applicant: SUNTORY HOLDINGS LIMITED, Osaka (JP)

(72) Inventors: Misa Ochiai, Osaka (JP); Jun Ogawa, Kyoto (JP); Eiji Sakuradani, Kyoto (JP); Akinori Ando, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 0 days.

(21) Appl. No.: 16/135,859

(22) Filed: Sep. 19, 2018

(65) Prior Publication Data

US 2019/0112613 A1    Apr. 18, 2019

Related U.S. Application Data

(62) Division of application No. 15/675,916, filed on Aug. 14, 2017, now Pat. No. 10,113,173, which is a division of application No. 14/779,080, filed as application No. PCT/JP2014/059698 on Mar. 26, 2014, now Pat. No. 9,765,345.

(30) Foreign Application Priority Data

Mar. 27, 2013    (JP) ................... 2013-066265

(51) Int. Cl.
   *C12N 1/20*    (2006.01)
   *C12N 15/80*   (2006.01)
   *C07K 14/37*   (2006.01)

(52) U.S. Cl.
   CPC ............ *C12N 15/80* (2013.01); *C07K 14/37* (2013.01); *H05K 999/99* (2013.01)

(58) Field of Classification Search
   CPC .................................................. C07K 14/37
   USPC .................................................. 435/254.11
   See application file for complete search history.

(56) References Cited

U.S. PATENT DOCUMENTS

2007/0072275 A1    3/2007    Ochiai et al.
2010/0203218 A1    8/2010    Ochiai et al.

FOREIGN PATENT DOCUMENTS

| CA | 1340433    | 3/1999  |
| EP | 2169055 A1 | 3/2010  |
| JP | 63-044891 A| 2/1988  |
| RU | 2340665    | 12/2008 |

OTHER PUBLICATIONS

International Search Report issued in PCT/JP2014/059698, dated Jul. 1, 2014, along with English language translation.
Mackenzie et al., "Isolation and Use of a Homologous Histone H4 Promoter and a Ribosomal DNA Region in a Transformation Vector for the Oil-Producing Fungus *Mortierella alpina*," *Applied and Environmental Microbiology*, vol. 66, No. 11, pp. 4655-4661, 2000.
Blazeck et al., "Tuning Gene Expression in *Yarrowia lipolytica* by a Hybrid Promoter Approach." *Applied and Evironmental Microbiology*, vol. 77, No. 22, pp. 7905-7914, 2011.
Okuda et al., "Selection and Characterization of Promoters Based on Genomic Approach for the Molecular Breeding of Oleaginous Fungus *Mortierella alpina* 1S-4," *Curr. Genet.*, published online Feb. 22, 2014 (9 pages).
Müller et al., "Comparison of Expression Systems in the Yeasts *Saccharomyces cerevisiae, Hansenula polymorpha, Klyveromyces lactis, Schizosaccharomyces pombe* and *Yarrowia lipolytica*. Cloning of Two Novel Promoters from *Yarrowia lipolytica*", *Yeast* 14, pp. 1267-1283, 1998.
Amarasinghe et al., "Genomic Approaches to the Discovery of Promoters for Sustained Expression in Cotton (*Gossypiun hirsutum* L.) under Field Conditions: Expression Analysis in Transgenic Cotton and *Arabidopsis* of a Rubisco Small Subunit Promoter Identified using EST Sequence Analysis and cDNA Microarrays," *Plant Biotechnology* 23, pp. 437-450, 2006.
Okuda et al., "Characterization of galactose-dependent promoters from an oleaginous fungus *Mortierella alpina* 1S-4," *Curr. Genet.*, vol. 60, pp. 175-182, 2014.
Park et al., "Galactose-inducible expression systems in *Candida maltosa* using promoters of newly-isolated GAL1 and GAL10 genes," *Yeast*, vol. 13, pp. 21-29, 1997.
Seiboth et al., "The *Hypocrea jecorina* gal10 (uridine 5'-diphosphate-glucose 4-epimerase-encoding) gene differs from yeast homologues in structure, genomic organization, and expression" *Gene*, vol. 295, pp. 143-149, 2002.
Extended European Search Report issued in EP Patent App. 14776138. 1, dated Nov. 14, 2016.
Russian Office Action dated Feb. 7, 2018 for corresponding Russian Application No. 2015-145333 with English-language translation.
Russian Search Report dated Feb. 7, 2018 in conjunction with the Office Action for corresponding Russian Application No. 2015-145333.

*Primary Examiner* — Tekchand Saidha
(74) *Attorney, Agent, or Firm* — Greenblum & Bernstein, P.L.C.

(57) ABSTRACT

The present invention aims to provide a promoter showing high expression activity in microorganisms belonging to the genus *Mortierella*. The present invention provides a polynucleotide which contains any one nucleotide sequence selected from the group consisting of SEQ ID NO: 1 to 28, or a variant thereof.

7 Claims, 13 Drawing Sheets
Specification includes a Sequence Listing.

Figure 12B

PROMOTER EXHIBITING HIGH EXPRESSION ACTIVITY IN *MORTIERELLA* MICROORGANISMS This application is a Divisional of U.S. patent application Ser. No. 15/675,916, filed Aug. 14, 2017, which is a Divisional of U.S. patent application Ser. No. 14/779,080, filed Sep. 22, 2015, now U.S. Pat. No. 9,765,345, which is the National Stage of International Patent Application No. PCT/JP2014/059698, filed Mar. 26, 2014, which claims the benefit of priority of Japanese Application No. 2013-066265, filed Mar. 27, 2013. The disclosures of these documents, including the specifications, drawings and claims, are incorporated herein by reference in their entirety.

TECHNICAL FIELD

The present invention provides a promoter showing high expression activity in cells of microorganisms belonging to the genus *Mortierella*, a vector comprising such a promoter, a non-human transformant transformed with such a promoter, as well as a method for production of proteins, lipids or fatty acids using such a promoter or transformant.

BACKGROUND OF THE INVENTION

Techniques to produce useful compounds through microbial metabolism (fermentation techniques in a broad sense) have been developed and used practically. For example, fungi of the genus *Mortierella* (e.g., *Mortierella alpina*) are known to produce polyunsaturated fatty acids (PUFAs) including arachidonic acid and are fungi particularly useful for industrial purposes (Patent Document 1).

For use of these fungi, breeding has been conducted, i.e., modifications have been made to improve the genetic traits of useful organisms (variety improvement). Particularly in fermentation techniques, breeding becomes very important in terms of improving the efficiency of microbial production of useful compounds and reducing the production costs of these compounds, etc.

To breed useful organisms having more desirable traits, transformation-based techniques are used. In this case, a DNA fragment encoding a protein necessary to acquire a desired trait is made expressible under the control of an appropriate gene promoter and then introduced into a useful organism to be bred (i.e., a host) to obtain a population of transformants. From among this population, a desired variety (strain) will then be selected. This procedure requires a gene promoter which is appropriate for the type of organism serving as a host or appropriate for the trait to be modified.

As to the transformation of filamentous fungi to which fungi of the genus *Mortierella* belong, many techniques have been reported. Moreover, in relation to the lipid production ability of fungi of the genus *Mortierella*, many enzyme genes involved in lipid synthesis systems have been obtained. However, there have been few reports about gene promoters required to introduce these useful enzyme genes into fungi of the genus *Mortierella* and to cause their expression at high levels.

PATENT DOCUMENTS

Patent Document 1: JP 63-044891 A

BRIEF SUMMARY OF THE INVENTION

Under these circumstances, there is a demand for the breeding of strains which produce useful lipids efficiently. For this purpose, gene promoters suitable for fungi of the genus *Mortierella* are required.

As a result of extensive and intensive efforts, the inventors of the present invention have succeeded in cloning a promoter for a gene highly expressed in *Mortierella alpina* (*M. alpina*), and thereby have completed the present invention. Namely, the present invention provides a polynucleotide, an expression vector, a transformant, and a method for production of proteins, lipids or fatty acids using such a polynucleotide or transformant, as shown below.

In more detail, the present invention is as follows.

[1] A polynucleotide of any one selected from the group consisting of (a) to (c) shown below:
 (a) a polynucleotide which contains any one nucleotide sequence selected from the group consisting of SEQ ID NOs: 1 to 28;
 (b) a polynucleotide which has a nucleotide sequence sharing an identity of 90% or more with any one nucleotide sequence selected from the group consisting of SEQ ID NOs: 1 to 28 and which shows promoter activity in cells of microorganisms belonging to the genus *Mortierella*; and
 (c) a polynucleotide which is hybridizable under stringent conditions with a polynucleotide consisting of a nucleotide sequence complementary to any one nucleotide sequence selected from the group consisting of SEQ ID NOs: 1 to 28 and which shows promoter activity in cells of microorganisms belonging to the genus *Mortierella*.

[2] The polynucleotide according to [1] above, wherein the promoter activity is confirmed as GUS protein activity of at least 500 nmol/(mg·min) upon expression of GUS reporter gene in cells of microorganisms belonging to the genus *Mortierella*.

[3] The polynucleotide according to [1] above, which contains any one nucleotide sequence selected from the group consisting of SEQ ID NOs: 1 to 28.

[4] The polynucleotide according to [1] or [2] above, which is DNA.

[5] A vector containing the polynucleotide according to any one of [1] to [4] above.

[6] A non-human transformant transformed with the polynucleotide according to any one of [1] to [4] above.

[7] A non-human transformant transformed with the vector according to [6] above.

[8] The transformant according to [7] or [8] above, wherein the transformant is a lipid-producing fungus.

[9] The transformant according to [8] above, wherein the lipid-producing fungus is *Mortierella alpina*.

When used as a promoter, the polynucleotide of the present invention allows highly efficient expression of a target gene in cells of microorganisms belonging to the genus *Mortierella*.

BRIEF DESCRIPTION OF THE DRAWINGS

FIG. 12B is continued from FIG. 12A.

DETAILED DESCRIPTION OF THE INVENTION

Figure 1:
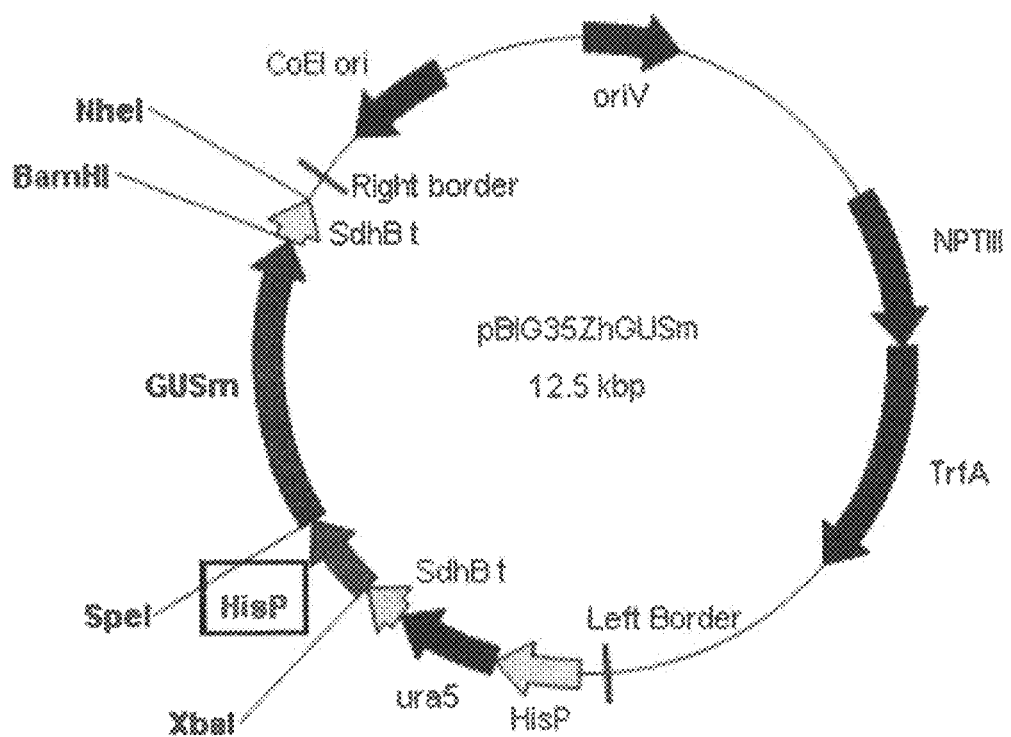
FIG. 1 shows an example of a vector for use in evaluation of the promoter of the present invention. The HisP sequence is replaced with the promoter of the present invention before use.

The present invention will be described in more detail below. The following embodiments are illustrated to describe the present invention, and it is not intended to limit the present invention only to these embodiments. The present invention can be implemented in various modes, without departing from the spirit of the present invention.

It should be noted that all publications cited herein, including prior art documents, patent gazettes and other patent documents, are incorporated herein by reference. Moreover, this specification incorporates the contents disclosed in the specification and drawings of Japanese Patent Application No. 2013-066265 (filed on Mar. 27, 2013), based on which the present application claims priority.

Unless otherwise specified herein, nucleotide sequences are shown such that their 5'-terminal end is on the left-hand side and their 3'-terminal end is on the right-hand side.

1. Promoters

The inventors of the present invention have succeeded, ahead of others, in cloning several types of promoter sequences from a lipid-producing fungus, *M. alpina*, as described in more detail later in the Example section. Moreover, the inventors of the present invention have also confirmed that proteins expressed under these promoters exert their biological activity.

Promoters according to the present invention are PP7p, CIT1p, PP3p, PP2p, PP6ps, HSC82p, SSA2p, GAL10-2p and/or partial sequences (truncated sequences) thereof. These promoter region sequences and truncated sequences thereof are shown in the table below.

Any one sequence selected from the nucleotide sequences shown in the table, i.e., any one sequence selected from the group consisting of SEQ ID NOs: 1 to 28 is hereinafter referred to as "the promoter sequence of the present invention."

TABLE 1

| Promoter sequence: Name (SEQ ID NO) | Truncated promoter sequence: Name (SEQ ID NO) | | | |
|---|---|---|---|---|
| PP7p (SEQ ID NO: 1) | PP7p D1000 (SEQ ID NO: 2) | PP7p D750 (SEQ ID NO: 3) | PP7p D500 (SEQ ID NO: 4) | |
| CIT1p (SEQ ID NO: 5) | CIT1p D1300 (SEQ ID NO: 6) | CIT1p D1000 (SEQ ID NO: 7) | CIT1p D700 (SEQ ID NO: 8) | CIT1p D400 (SEQ ID NO: 9) |
| PP3p (SEQ ID NO: 10) | PP3p D1600 (SEQ ID NO: 11) | PP3p D1200 (SEQ ID NO: 12) | | |
| PP2p (SEQ ID NO: 13) | | | | |
| PP6p (SEQ ID NO: 14) | PP6p D1000 (SEQ ID NO: 15) | PP6p D750 (SEQ ID NO: 16) | | |
| HSCB2p (SEQ ID NO: 17) | HSC82p D800 (SEQ ID NO: 18) | HSC82p D600 (SEQ ID NO: 19) | HSC82p D400 (SEQ ID NO: 20) | HSC82p D200 (SEQ ID NO: 21) |
| SSA2p (SEQ ID NO: 22) | SSA2p D850 (SEQ ID NO: 23) | SSA2p D600 (SEQ ID NO: 24) | SSA2p D400 (SEQ ID NO: 25) | SSA2p D200 (SEQ ID NO: 26) |
| GAL10-2p (SEQ ID NO: 27) | GAL10-2p D2000 (SEQ ID NO: 28) | | | |

Thus, the present invention provides the following polynucleotide as a promoter showing high expression activity in cells of microorganisms belonging to the genus *Mortierella*.

A polynucleotide of any one selected from the group consisting of (a) to (c) shown below:

(a) a polynucleotide which contains the promoter sequence of the present invention;

(b) a polynucleotide which has a nucleotide sequence sharing an identity of 90% or more with the promoter sequence of the present invention and which shows promoter activity in cells of microorganisms belonging to the genus *Mortierella*; and (c) a polynucleotide which is hybridizable under stringent conditions with a polynucleotide consisting of a nucleotide sequence complementary to the promoter sequence of the present invention and which shows promoter activity in cells of microorganisms belonging to the genus *Mortierella*.

The above polynucleotides shown in (a) to (c) are each hereinafter referred to as "the polynucleotide of the present invention."

Moreover, in the context of the present invention, "having" the promoter sequence of the present invention means "comprising" the promoter sequence of the present invention. Thus, an additional sequence(s) (e.g., an enhancer sequence) other than the promoter sequence of the present invention may be added to the upstream (5'-terminal side) or downstream (3'-terminal side) of the promoter sequence of the present invention. Such an additional sequence may be added to the promoter sequence of the present invention via a nucleotide sequence of 1 to 1000 bp, 1 to 900 bp, 1 to 800 bp, 1 to 700 bp, 1 to 600 bp, 1 to 500 bp, 1 to 400 bp, 1 to 300 bp, 1 to 200 bp, 1 to 100 bp, 1 to 75 bp, 1 to 50 bp, 1 to 25 bp or 1 to 10 bp, or alternatively, may be directly added to the promoter sequence of the present invention (i.e., the number of nucleotide residues located between the promoter sequence of the present invention and the additional sequence is zero).

As used herein, the term "polynucleotide" is intended to mean DNA or RNA.

As used herein, the expression "polynucleotide which is hybridizable under stringent conditions" is intended to mean, for example, a polynucleotide that can be obtained by means of, e.g., colony hybridization, plaque hybridization or Southern hybridization using, as a probe, the whole or a part of a polynucleotide consisting of a nucleotide sequence complementary to the promoter sequence of the present invention. For hybridization, it is possible to use techniques as described in, e.g., "Sambrook & Russell, Molecular Cloning: A Laboratory Manual Vol. 3, Cold Spring Harbor, Laboratory Press 2001" and "Ausubel, Current Protocols in Molecular Biology, John Wiley & Sons 1987-1997."

As used herein, the term "high stringent conditions" is intended to mean, for example, conditions of (1) 5×SSC, 5×Denhardt's solution, 0.5% SDS, 50% formamide and 50° C., (2) 0.2×SSC, 0.1% SDS and 60° C., (3) 0.2×SSC, 0.1% SDS and 62° C., (4) 0.2×SSC, 0.1% SDS and 65° C., or (5) 0.1×SSC, 0.1% SDS and 65° C., without being limited thereto. Under these conditions, it can be expected that DNA having a higher sequence identity is more efficiently obtained at a higher temperature. However, the stringency of hybridization would be affected by a plurality of factors, including temperature, probe concentration, probe length, ionic strength, reaction time, salt concentration and so on. Those skilled in the art would be able to achieve the same stringency by selecting these factors as appropriate.

It should be noted that if a commercially available kit is used for hybridization, an Alkphos Direct Labelling and Detection System (GE Healthcare) may be used for this purpose, by way of example. In this case, hybridization may be accomplished in accordance with the protocol attached to the kit, i.e., a membrane may be incubated overnight with a labeled probe and then washed with a primary washing buffer containing 0.1% (w/v) SDS under conditions of 55° C. to detect the hybridized DNA. Alternatively, if a commercially available reagent (e.g., PCR labeling mix (Roche Diagnostics)) is used for digoxigenin (DIG) labeling of a probe during probe preparation based on the whole or a part of a nucleotide sequence complementary to the promoter sequence of the present invention, a DIG nucleic acid detection kit (Roche Diagnostics) may be used for detection of hybridization.

In addition to those listed above, other hybridizable polynucleotides include polynucleotides sharing an identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with the promoter sequence of the present invention, as calculated by homology search software such as FASTA or BLAST using default parameters.

It should be noted that the identity of nucleotide sequences can be determined by using FASTA (Science 227 (4693): 1435-1441, (1985)) or the algorithm of Karlin and Altschul, BLAST (Basic Local Alignment Search Tool) (Proc. Natl. Acad. Sci. USA 872264-2268, 1990; Proc Natl Acad Sci USA 90: 5873, 1993). Based on the algorithm of BLAST, programs called blastn, blastx, tblastn and tblastx have been developed (Altschul S F, et al: J Mol Biol 215: 403, 1990). If blastn is used for nucleotide sequence analysis, parameters may be set to, for example, score=100 and wordlength=12. If BLAST and Gapped BLAST programs are used, default parameters in each program may be used.

In the context of the present invention, the term "promoter activity" is intended to mean that when a protein-encoding gene sequence (hereinafter referred to as a "target gene") is inserted downstream of the promoter of the present invention, an expression product of this gene is obtained.

The term "expression product" used here is intended to mean either or both of RNA (e.g., hnRNA, mRNA, siRNA or miRNA) which is a transcribed product of the gene and a protein which is a translated product of the gene.

Insertion of a target gene may be accomplished such that the 5'-terminal end of the target gene is located in a region within 500 bp, 400 bp, 300 bp, 200 bp, 100 bp, 50 bp, 30 bp or 10 bp from the 3'-terminal end of the promoter sequence of the present invention.

In the case of attempting to confirm the activity of the promoter sequence of the present invention, the target gene is not limited in any way, but is preferably a gene encoding a protein whose activity can be measured by the established method.

Examples of such a gene include, but are not limited to, selection marker genes such as neomycin resistance gene, hygromycin B phosphotransferase gene and so on, as well as expression reporter genes such as LacZ, GFP (Green Fluorescence Protein) and luciferase genes, etc.

Preferably, confirmation of promoter activity may be accomplished by using a gene for β-D-glucuronidase (GUS) to measure GUS activity. In cases where *M. alpina* is used as a host, the GUS gene is preferably a GUSm gene whose codon usage frequency has been adapted to *M. alpina*.

GUS activity can be measured as follows: the promoter sequence of the present invention is used to cause GUS gene expression in cells of microorganisms belonging to the genus *Mortierella*, the GUS protein collected from the above cells is then reacted with p-nitrophenyl-β-D-glucuronide, and the reaction system is measured over time for absorbance at a wavelength of 405 nm, followed by calculation from the measured values according to the following equation.

GUS activity (nmol/(mg·min))=1000×[(gradient value in the absorbance versus time graph obtained for each sample)/(gradient value in the calibration graph)]/[(protein concentration in the sample)/5]

The GUS gene used for this purpose is generally the *E. coli*-derived GUS gene (CDS sequence: SEQ ID NO: 29, amino acid sequence: SEQ ID NO: 30). In cases where the promoter sequence of the present invention is used to cause GUS gene expression in cells of microorganisms belonging to the genus *Mortierella*, a GUSm gene (CDS sequence: SEQ ID NO: 31, amino acid sequence: SEQ ID NO: 32) may be used, which has been modified such that the codon usage in the *E. coli*-derived GUS gene is adapted to microorganisms of the genus *Mortierella*.

Figure 12A:
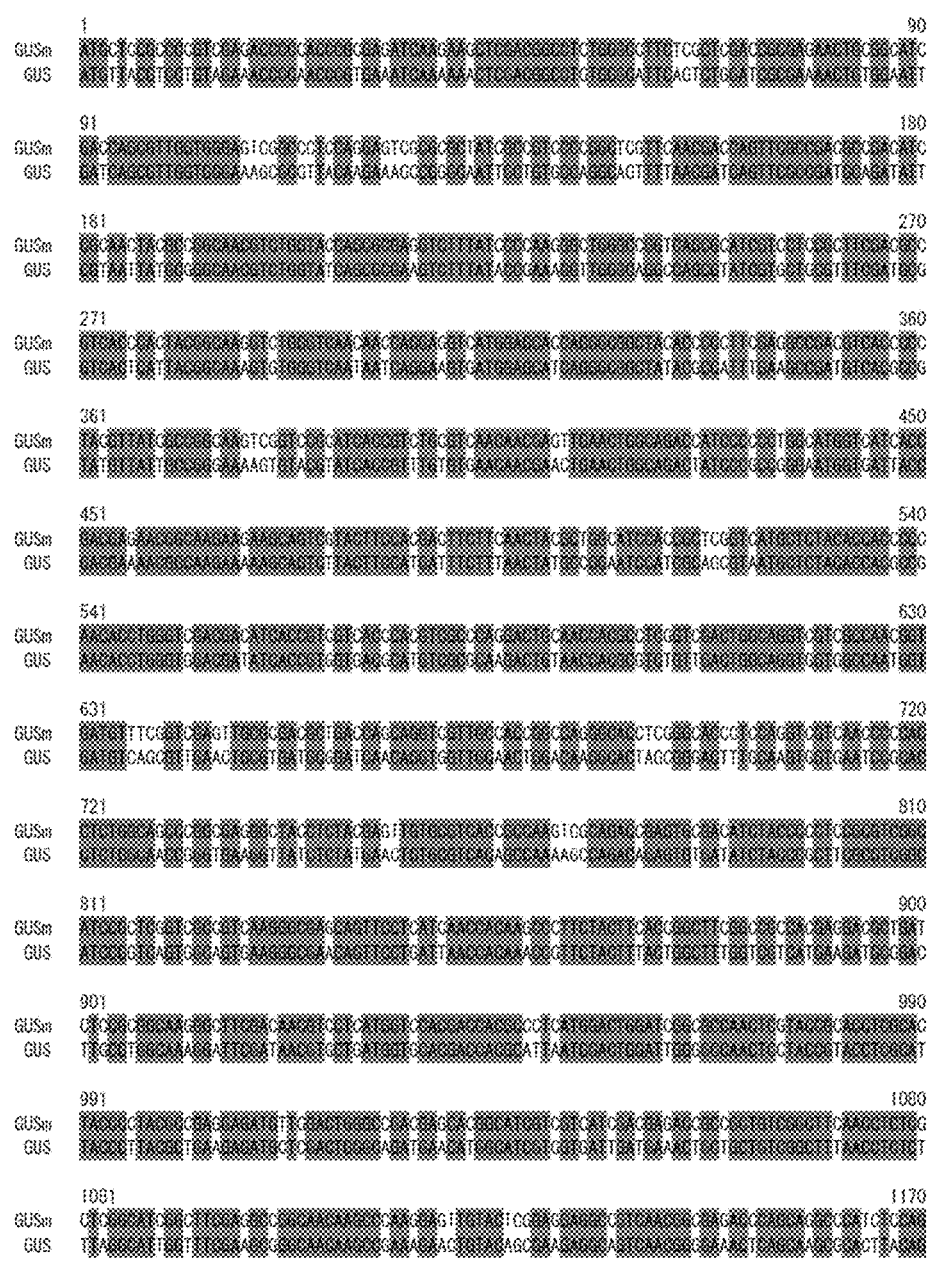
FIG. 12A shows an alignment between *E. coli*-derived GUS gene (CDS sequence: SEQ ID NO: 29, amino acid sequence: SEQ ID NO: 30) and GUSm gene (CDS sequence: SEQ ID NO: 31, amino acid sequence: SEQ ID NO: 32) which has been modified such that the codon usage in the *E. coli*-derived GUS gene is adapted to microorganisms of the genus *Mortierella*.
Figure 12B:
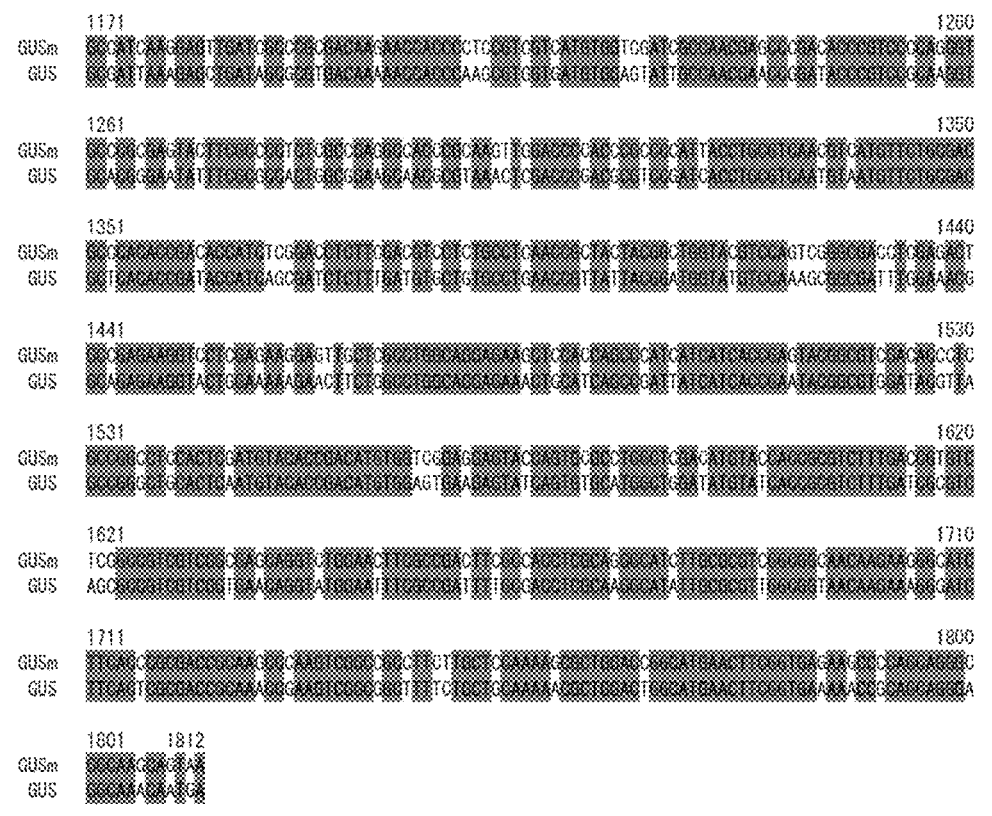

As for examples of codon usage modification, reference may be made to the alignment between GUSm and GUS shown in FIG. 12A and FIG. 12B.

The promoter activity in the present invention is preferably intended to give GUS protein activity of at least 500, 600, 700, 800, 900, 1000, 1200, 1400, 1600, 1800 or 2000 nmol/(mg·min) upon expression of the GUS reporter gene in cells of microorganisms belonging to the genus *Mortierella* as described above.

Procedures for gene transfer into host cells are as described later.

The polynucleotide of the present invention mentioned above can be obtained by known genetic engineering procedures or known synthesis procedures.

2. Vectors and Transformants

In another embodiment, the present invention also provides an expression vector containing the polynucleotide of the present invention (hereinafter referred to as "the vector of the present invention").

The vector of the present invention is generally configured to comprise:
(i) the promoter of the present invention; and
(ii) an expression cassette comprising, as constituent elements, signals that function in host cells for transcription termination and polyadenylation of an RNA molecule.

The thus configured vector is introduced into host cells. Examples of appropriate host cells used in the present invention include lipid-producing fungi, yeast and so on.

As lipid-producing fungi, strains as found in MYCOTAXON, Vol. XLIV, No. 2, pp. 257-265 (1992) can be used. Specific examples include microorganisms belonging to the genus *Mortierella*, as exemplified by microorganisms belonging to the subgenus *Mortierella* such as *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS 219.35, CBS224.37, CBS250.53, CBS343.66, CBS527.72, CBS528.72, CBS529.72, CBS608.70, CBS754.68, etc., as well as microorganisms belonging to the subgenus *Micromucor* such as *Mortierella isabellina* CBS194.28, IFO6336, IFO7824, IFO07873, IFO7874, IFO08286, IFO8308, IFO7884, *Mortierella nana* IFO8190, *Mortierella raanniana* IFO5426, IFO8186, CBS112.08, CBS212.72, IFO7825, IFO8184, IFO8185, IFO8287, *Mortierella vinacea* CBS236.82, etc. Particularly preferred is *Mortierella alpina*.

Such a vector may be prepared starting from an existing expression vector, e.g., pDura5 (Appl. Microbiol. Biotechnol., 65, 419-425, (2004)), pBIG35 (Appl. Environ. Microbiol., (2009), vol. 75, p. 5529-5535), pD4 (Appl. Environ. Microbiol., November 2000, 66(11), p. 4655-4661), pDZeo (J. Biosci. Bioeng., December 2005, 100(6), p. 617-622), pDX vector (Curr. Genet., 2009, 55(3), p. 349-356) or pBIG3ura5 (Appl. Environ. Microbiol., 2009, 75, p. 5529-5535) by replacement of the promoter region in the starting expression vector with the promoter sequence of the present invention, although the starting expression vector is not limited to the above vectors.

For transformation of host cells, a selection marker may be used to confirm whether the vector has been introduced. Examples of a selection marker available for use include auxotrophic markers (ura5, niaD, trp1), drug resistance markers (hygromycine, zeocin), geneticin resistance gene (G418r), copper resistance gene (CUP1) (Marin et al., Proc. Natl. Acad. Sci. USA, 81, 337 1984), cerulenin resistance genes (fas2m, PDR4) (Junji Inokoshi et al., Biochemistry, vol. 64, p. 660, 1992; Hussain et al., gene, 101, 149, 1991), etc.

Examples of auxotrophic markers include, but are not limited to, (1) to (15) shown below:
(1) methionine auxotrophic marker: met1, met2, met3, met4, met5, met6, met7, met8, met10, met13, met14 or met20;
(2) tyrosine auxotrophic marker: tyr1 or isoleucine;
(3) valine auxotrophic marker: ilv1, ilv2, ilv3 or ilv5;
(4) phenylalanine auxotrophic marker: pha2;
(5) glutamic acid auxotrophic marker: glu3;
(6) threonine auxotrophic marker: thr1 or thr4;
(7) aspartic acid auxotrophic marker: asp1 or asp5;
(8) serine auxotrophic marker: ser1 or ser2;
(9) arginine auxotrophic marker: arg1, arg3, arg4, arg5, arg8, arg9, arg80, arg81, arg82 or arg84;
(10) uracil auxotrophic marker: ura1, ura2, ura3, ura4, ura5 or ura6;
(11) adenine auxotrophic marker: ade1, ade2, ade3, ade4, ade5, ade6, ade8, ade9, ade12 or ADE15;
(12) lysine auxotrophic marker: lys1, lys2, lys4, lys5, lys7, lys9, lys11, lys13 or lys14;
(13) tryptophan auxotrophic marker: trp1, trp2, trp3, trp4 or trp5;
(14) leucine auxotrophic marker: leu1, leu2, leu3, leu4 or leu5; and
(15) histidine auxotrophic marker: his1, his2, his3, his4, his5, his6, his7 or his8.

Examples of drug resistance markers include, but are not limited to, hygromycin (Hygromycin B) resistance gene, bleomycin t (pleomycin) resistance gene (Transformation of filamentous fungi based on hygromycin b and phleomycin resistance markers, Methods in Enzymology, Volume 216, 1992, Pages 447-457, Peter J. Punt, Cees A. M. J. J. van den Hondel), bialaphos resistance gene (Avalos, J., Geever, R. F., and Case, M. E. 1989. Bialaphos resistance as a dominant selectable marker in *Neurospora crassa*. Curr. Genet. 16: 369-372), sulfonylurea resistance gene (Zhang, S., Fan, Y., Xia, Y. X., and Keyhani, N. O. (2010) Sulfonylurea resistance as a new selectable marker for the entomopathogenic fungus *Beauveria bassiana*. Appl Microbiol Biotechnol 87: 1151-1156), benomyl resistance gene (Koenraadt, H., S. C. Sommerville, and A. L. Jones. 1992. Characterization of mutations in the beta-tubulin gene of benomyl-resistant field strains of *Venturia inaequalis* and other pathogenic fungi. Mol. Plant Pathol. 82:1348-1354), acetamide assimilation gene (Acetamidase, AmdS) (Kelly, J. M. and Hynes, M. J. (1985). Transformation of *Aspergillus niger* by the Eamds gene of *Aspergiilus nidulans*. EMBO J. 4, 475-479), etc.

For transformation of host cells, commonly used known techniques can be used. For example, in the case of lipid-producing fungi, it is possible to use electroporation (Mackenxie D. A. et al. Appl. Environ. Microbiol., 66, 4655-4661, 2000), particle delivery method (descried in JP 2005-287403 A entitled "Breeding Method of Lipid Producing Fungi") or *Agrobacterium*-mediated method, without being limited thereto.

In addition, as for standard cloning techniques, reference may be made to "Sambrook & Russell, Molecular Cloning: A Laboratory Manual VoL 3, Cold Spring Harbor Laboratory Press 2001" and "Methods in Yeast Genetics, A laboratory manual (Cold Spring Harbor Laboratory Press, Cold Spring Harbor, N.Y.)," etc.

3. Method for Production of Proteins, Lipids or Fatty Acids

In yet another embodiment, the present invention also provides a method for production of proteins, lipids or fatty acids using the above transformant.

A target gene is highly expressed in a non-human transformant transformed with the promoter of the present invention (hereinafter referred to as "the transformant of the present invention"), particularly prepared using a microorganism belonging to the genus *Mortierella* as a host cell. Thus, when using the transformant of the present invention, a target protein can be produced efficiently.

For example, a target gene is operably introduced into the vector of the present invention and a transformant transformed with this vector is cultured, whereby a target protein can be expressed from the target gene in cells of the transformant.

The expressed target protein may be collected, for example, by preparing a cell lysate from the transformant and treating this lysate in accordance with known procedures. For details of target protein collection, reference may be made to "Sambrook & Russell, Molecular Cloning: A Laboratory Manual Vol. 3, Cold Spring Harbor Laboratory Press 2001" and "Methods in Yeast Genetics, A laboratory manual (Cold Spring Harbor Laboratory Press, Cold Spring Harbor, N.Y.)," etc.

The target gene is not limited in any way, but is preferably a gene encoding a lipid synthase (hereinafter referred to as a "lipid synthase gene"). Examples include genes encoding acyl-CoA synthase, glycerol-3-phosphate acyltransferase, diacylglycerol acyltransferase, fatty acid elongase, Δ9 fatty acid desaturase gene, Δ12 fatty acid desaturase gene, Δ6 fatty acid desaturase gene, Δ5 fatty acid desaturase gene, Δ4 fatty acid desaturase gene, ω3 fatty acid desaturase gene, lysophospholipid acyltransferase gene, phosphatidic acid phosphatase gene, fatty acid synthase gene, acetyl-CoA carboxylase gene, and ATP:citrate lyase gene.

When cells with lipid synthesis ability, e.g., a lipid-producing fungus or the like is used as a host to express a lipid synthase gene, the lipid synthase expressed from this gene causes synthesis of lipids and/or fatty acids, which may then be collected. Thus, upon culturing the transformant of the present invention, it is possible to produce lipids and/or fatty acids with high efficiency.

Lipids or fatty acids can be extracted as follows from cells which have been transformed in accordance with the present invention. After being cultured, a transformed strain of an organism (e.g., lipid-producing fungus or yeast) is treated in a standard manner, e.g., by centrifugation or filtration to obtain cultured cells. The cells are washed well with water and preferably further dried. Drying may be accomplished by freeze-drying, air-drying, etc. The dried cells are optionally homogenized, e.g., with a Dynomil or by ultrasonication, and then extracted with an organic solvent preferably under a nitrogen stream. Organic solvents used for this purpose include ether, hexane, methanol, ethanol, chloroform, dichloromethane, petroleum ether and so on. Alternatively, good results can also be obtained by alternating extraction with methanol and petroleum ether or by extraction with a single-phase solvent system of chloroform-methanol-water. When the organic solvent is distilled off from the extract under reduced pressure, fatty acid-containing lipids can be obtained. The extracted fatty acids may be converted into corresponding methyl esters by the hydrochloric acid-methanol method, etc.

Moreover, fatty acids can be separated in a state of mixed fatty acids or mixed fatty acid esters from the above fatty acid-containing lipids by concentration and separation in a standard manner (e.g., urea addition, separation under cooling, column chromatography).

EXAMPLES

The present invention will now be described in more detail by way of the following examples, which are not intended to limit the scope of the present invention.

Genomic Analysis of *Mortierella alpina*

*M. alpina* strain 1S-4 was inoculated into 100 ml of GY2:1 medium (2% glucose, 1% yeast extract, pH 6.0) and cultured at 28° C. for 2 days under shaking conditions. The cells were collected by filtration, and their genomic DNA was prepared using DNeasy (QIAGEN).

The nucleotide sequence of the above genomic DNA was determined using a Roche 454 GS FLX Standard, during which nucleotide sequencing was conducted in two runs for a fragment library and in three runs for a mate-paired library. The resulting nucleotide sequences were assembled to give 300 super contigs.

Expression Analysis

*M. alpina* strain 1S-4 was inoculated into 100 ml of a medium (1.8% glucose, 1% yeast extract, pH 6.0) and pre-cultured for 3 days at 28° C. A 10 L culture vessel (Able Co., Tokyo) was charged with 5 L of a medium (1.8% glucose, 1% soybean meal, 0.1% olive oil, 0.01% Adekanol, 0.3% $KH_2PO_4$, 0.1% $Na_2SO_4$, 0.05% $CaCl_2.2H_2O$, 0.05% $MgCl_2.6H_2O$, pH 6.0) and inoculated with the entire pre-cultured product, followed by aerobic spinner culture under conditions of 300 rpm, 1 vvm and 26° C. for 8 days. On days 1, 2 and 3 of culture, glucose was added in an amount corresponding to 2%, 2% and 1.5%, respectively. The cells were collected at each stage of culture (day 1, 2, 3, 6 or 8) to prepare total RNA by the guanidine hydrochloride/CsCl method. Using SOLiD™ Total RNA-Seq for Whole Transcriptome Libraries (Applied Biosystems), cDNA was synthesized for each stage and sequenced in SOLiD.

Cloning of Promoter Regions

Cloning was performed as follows on promoter regions in genes whose expression levels were considered to be high in *M. alpina* strain 1S-4 in light of the results of expression analysis or a promoter region in a homolog of the galactose metabolic system gene.

First, primers required for PCR amplification of each promoter region were designed as follows. It should be noted that the underlined parts in the nucleotide sequences of primers shown below each represent a restriction enzyme recognition site. Primers were designed such that XbaI and SpeI recognition sequences were added respectively to both ends of the promoter region. However, only for GAL10-2p which has a SpeI recognition sequence in its sequence, primers were designed such that an XbaI recognition sequence was added to each end. The symbol "F" or "R" appearing in each primer name denotes that the primer is a forward primer or a reverse primer, respectively.

```
Promoter PP7p
PP7p F XbaI
                                  (SEQ ID NO: 33)
AATATCTAGATGACCGTGCGCTTTTTGAGAC PP7p R SpeI
                                  (SEQ ID NO: 34)
AGCAACTAGTCGTATATTTGTTGAAAGGTG Promoter CIT1p
CIT1p F XbaI
                                  (SEQ ID NO: 35)
ATTTTCTAGACACCTCAAAAACGTGCCTTG
```

```
CIT1 p R SpeI
                                        (SEQ ID NO: 36)
AATAACTAGTGGCGGATATGTGTATGGAG

Promoter PP3p
PP3p F XbaI
                                        (SEQ ID NO: 37)
AACGTCTAGACGTGTTATCTTGCGCTGC PP3p R SpeI
                                        (SEQ ID NO: 38)
TCATACTAGTGATGATTTAGAGGTGTTGG Promoter PP2p
PP2p F XbaI
                                        (SEQ ID NO: 39)
AAGCTCTAGAGACTGTAAAGACGGAGGGG PP2p R SpeI
                                        (SEQ ID NO: 40)
AGTAACTAGTTGTGGATAGTGGGTAGTGG Promoter PP6ps
PP6ps F XbaI
                                        (SEQ ID NO: 41)
AAAGTCTAGACTGGCAATAGTTAGTGCACG PP6ps R SpeI
                                        (SEQ ID NO: 42)
ATCAACTAGTGATGGAGGTTTGTTTGAGAAG Promoter HSC82p
HSC82p F XbaI
                                        (SEQ ID NO: 43)
ATCATCTAGAGAGCTCAAGATGAAGGTGCTC HSC82p R SpeI
                                        (SEQ ID NO: 44)
AATAACTAGTGGTGTGTGGTTTGCGGG Promoter SSA2p
SSA2p F XbaI
                                        (SEQ ID NO: 45)
TTAGTCTAGAAAAGTGCTGCTTCGGAACC SSA2p R SpeI
                                        (SEQ ID NO: 46)
AGATACTAGTGATGTAGATGTGAGTGTGAG Promoter GAL10-2p
GAL10-2p F XbaI
                                        (SEQ ID NO: 47)
AATATCTAGAGGTTCCGAGAGGTGGATTTG GAL10-2p R XbaI
                                        (SEQ ID NO: 48)
ATAATCTAGATGGCTCCTGAAAGGACGAG
```

Using the genome of *Mortierella alpina* strain 1S-4 as a template, each promoter region was cloned by PCR. The polymerase used was PrimeSTAR GXL (TaKaRa).

Vector Construction for Promoter Evaluation

GUSm gene (SEQ ID NO: 31) which had been modified such that the codon usage in the *E. coli*-derived GUS gene (SEQ ID NO: 29) was adapted to microorganisms of the genus *Mortierella* (FIG. 12A and FIG. 12B) was used as a reporter gene.

GUSm was ligated to plasmid pBIG35 containing histone promoter (HisP) serving as a constitutive expression promoter (Appl. Environ. Microbiol., (2009), vol. 75, p. 5529-5535) to construct an expression cassette. This expression cassette was further ligated in tandem to a uracil auxotrophic marker gene (ura5) to construct a binary vector for transformation, pBIG35ZhGUSm (FIG. 1). It should be noted that the GUSm gene used in the vector is an artificially synthesized β-D-glucuronidase gene whose codon usage frequency has been adapted to *M. alpina*. Ura5 is the *M. alpina* orotate phosphoribosyltransferase gene. HisP is a promoter for the *M. alpina* histone H4.1 gene. SdhBt is a terminator for the *M. alpina* succinate dehydrogenase gene. ColE1 ori is the origin of replication, NPTII is a kanamycin resistance gene, TrfA is a gene responsible for plasmid amplification, and Left and Right borders are repeat sequences for gene transfer.

The promoter regions cloned as described above were each excised with restriction enzymes XbaI and SpeI or with a restriction enzyme XbaI, and then inserted in place of HisP into the XbaI- and SpeI-digested vector pBIG35ZhGUSm.

Transformation of *Mortierella alpina*

A uracil auxotrophic strain (Δura-3) was induced from *M. alpina* strain 1S-4 in accordance with procedures described in a patent document (WO2005/019437) and cultured on 0.05 mg/mL uracil-containing Czapek-Dox agar medium (3% sucrose, 0.2% $NaNO_3$, 0.1% $KH_2PO_4$, 0.05% KCl, 0.05% $MgSO_4 \cdot 7H_2O$, 0.001% $FeSO_4 \cdot 7H_2O$, 2% agar, pH 6.0). The cultured product thus obtained was collected and filtered through Miracloth (Calbiochem) to prepare a spore suspension of *M. alpina* Δura-3. *Agrobacterium* (*Agrobacterium tumefaciens* C58C1) was transformed with each of the prepared vectors for promoter evaluation by electroporation and cultured at 28° C. for 48 hours on LB-Mg agar medium (1% tryptone, 0.5% yeast extract, 85 mM NaCl, 0.5 mM $MgSO_4 \cdot 7H_2O$, 0.5 mM NaOH, 1.5% agar, pH 7.0). *Agrobacterium* transformants carrying the vectors were confirmed by PCR. *Agrobacterium* transformants carrying the vectors were cultured at 28° C. at 120 rpm for 2 days under shaking conditions in 100 mL of MM medium (10 mM $K_2HPO_4$, 10 mM $KH_2PO_4$, 2.5 mM NaCl, 2 mM $MgSO_4 \cdot 7H_2O$, 0.7 mM $CaCl_2$, 9 μM $FeSO_4 \cdot 7H_2O$, 4 mM $(NH_4)_2SO_4$, 10 mM glucose, pH 7.0), centrifuged at 5,800×g and then diluted with fresh IM medium (MM medium supplemented with 0.5% glycerol, 200 μM acetosyringone and 40 mM 2-(N-morpholino)ethanesulfonic acid (MES) and adjusted to pH 5.3) to prepare suspensions. These suspensions were cultured for 8 to 12 hours at 28° C. at 300 rpm under shaking conditions to reach OD 660=0.4 to 3.7. Each of the cell suspensions (100 μL) was mixed with an equal volume of the above *M. alpina* Δura-3 suspension ($10^8$ $mL^{-1}$), spread onto a nitrocellulose membrane (70 mm diameter; hardened low-ash grade 50, Whatman) placed on a co-culture medium (having the same composition as IM medium, except for containing 5 mM glucose instead of 10 mM glucose and 1.5% agar) and then cultured at 23° C. for 2 to 5 days. After co-culture, the membrane was transferred onto uracil-free and 0.03% Nile blue A (Sigma)-containing SC agar medium (5.0 g Yeast Nitrogen Base w/o Amino Acids and Ammonium Sulfate (Difco), 1.7 g $(NH_4)_2SO_4$, 20 g glucose, 20 mg adenine, 30 mg tyrosine, 1.0 mg methionine, 2.0 mg arginine, 2.0 mg histidine, 4.0 mg lysine, 4.0 mg tryptophan, 5.0 mg threonine, 6.0 mg isoleucine, 6.0 mg leucine, 6.0 mg phenylalanine, 20 g/L agar) and cultured at 28° C. for 5 days. Hyphae from visible fungal colonies were transferred onto uracil-free SC medium. Transfer onto fresh uracil-free SC medium was repeated twice to thereby select transformants stably retaining their traits.

Selection of High Expression Promoters

Culture and Collection of Strains

Each transformant was cultured at 28° C. for 2 days on GY agar medium (2% glucose, 1% yeast extract, 1.5% agar). After completion of the culture, the cells were collected by being scraped off together with the agar.

Protein Extraction from Cells

The collected cells were mixed with 500 μL of a homogenization buffer (100 mM Tris-HCl (pH 8.0), 5 mM 2-mercaptoethanol) and homogenized twice at 5000 rpm for 30 seconds with a TOMY beads shocker using glass beads of 0.1 mm diameter. The homogenate was centrifuged at 8000×g for 10 minutes and the collected supernatant was further centrifuged at 20400×g for 10 minutes to collect the supernatant as a protein solution. The collected solution was measured for its protein concentration and optionally diluted to any concentration with the homogenization buffer. The foregoing operations were all conducted on ice.

GUS Activity Measurement

A substrate (p-nitrophenyl-β-D-glucuronide) was dissolved in an assay buffer (21.7 mM NaH$_2$PO$_4$, 33.9 mM Na$_2$HPO$_4$, 1.11 mM EDTA (pH 8.0)) to give a final concentration of 1.25 mM. This substrate solution (160 μL) and each protein sample (40 μL) were mixed on a 96-well microtiter plate, and the absorbance at 405 nm was measured over time at 37° C. The absorbance of p-nitrophenol was measured at 0.05 mM, 0.1 mM, 0.2 mM and 0.5 mM to prepare a calibration curve, and the value of GUS activity in each sample was calculated according to the following equation.

GUS activity (nmol/(mg·min))=1000×[(gradient value in the absorbance versus time graph obtained for each sample)/(gradient value in the calibration graph)]/[(protein concentration in the sample)/5]

The amount (nmol) of p-nitrophenyl-β-D-glucuronide converted into p-nitrophenol by the action of 1 mg/mL protein for 1 minute is defined as 1 unit of GUS activity.

Selection of Strains for GUS Activity Evaluation

The stable transformed strains (30 strains) selected for evaluation of each promoter were cultured on GY agar medium as described above and measured for their GUS activity. From among these 30 strains, 10 strains showing moderate GUS activity were selected.

Evaluation of Promoter Activity

Figure 2:
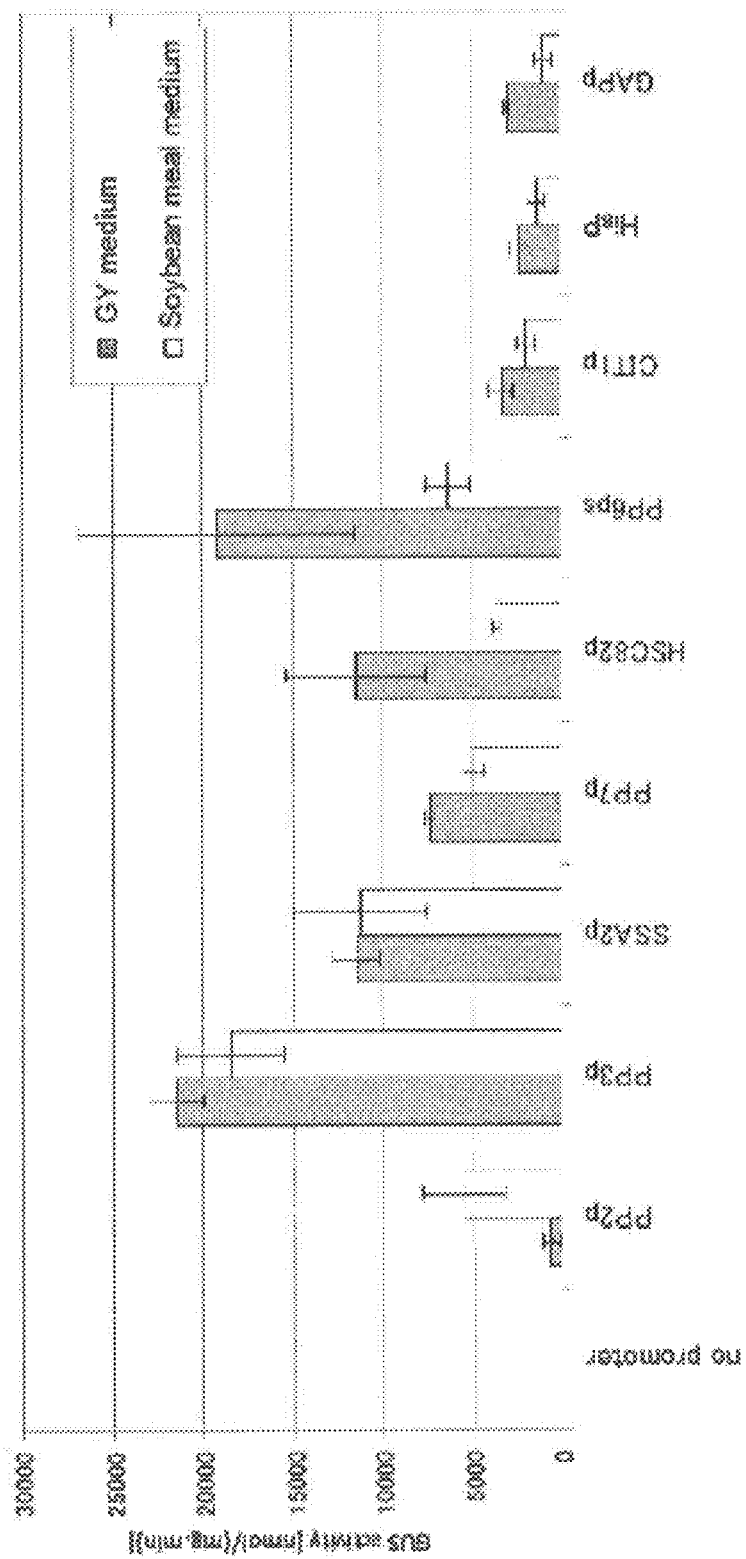
FIG. 2 shows the promoter activity in transformants transformed with the promoter sequences of the present invention upon culture in various media (gray bar: GY medium, white bar: soybean meal medium). Culture was conducted in each medium (10 ml) at 28° C. at 300 rpm for κ days.

The selected strains were cultured at 28° C. at 300 rpm for 5 days under shaking conditions in GY liquid medium (10 ml) or soybean meal medium (10 ml). After completion of the culture, the cells were collected by filtration and measured for their GUS activity. The mean of the measured values was evaluated as the activity of the promoter. The results obtained are shown in FIG. 2.

The evaluated promoters were found to have higher promoter activity than known *Mortierella*-derived promoters, HisP and GAPp, in the GY medium and/or in the soybean meal medium.

Study on Culture Time and the Activity of Each Promoter

To determine culture time-induced changes in promoter activity, the strains selected for each promoter were cultured at 28° C. under shaking conditions in GY liquid medium (10 ml) for 2 days, 5 days, 7 days or 14 days. After completion of the culture, the cells were collected by filtration and measured for their GUS activity. The results obtained are shown in the table below.

TABLE 2

Number of days for culture and activity of each promoter

| Promoter name | GUS activity (nmol/(min · mg$_{protein}$)) | | | |
|---|---|---|---|---|
| | 2 days | 5 days | 7 days | 14 days |
| PP7p | 10000 | | 10000 | 10000 |
| CIT1p | 7000 | | 2000 | 1000 |
| PP3p | 2500 | | 28000 | 30000 |
| PP2p | 1000 | | 1000 | 4500 |

TABLE 2-continued

Number of days for culture and activity of each promoter

| Promoter name | GUS activity (nmol/(min · mg$_{protein}$)) | | | |
|---|---|---|---|---|
| | 2 days | 5 days | 7 days | 14 days |
| PP6p | 10000 | 20000 | | 2500 |
| HSC82p | 10000 | | 10000 | 6000 |
| SSA2p | 12000 | | 10000 | 14000 |
| GAPp | 3000 | | 2500 | 2500 |
| HisP | 2500 | | 2500 | 2500 |

Evaluation of Inducible Promoter

Promoter GAL10-2p was evaluated as follows.

Figure 3:
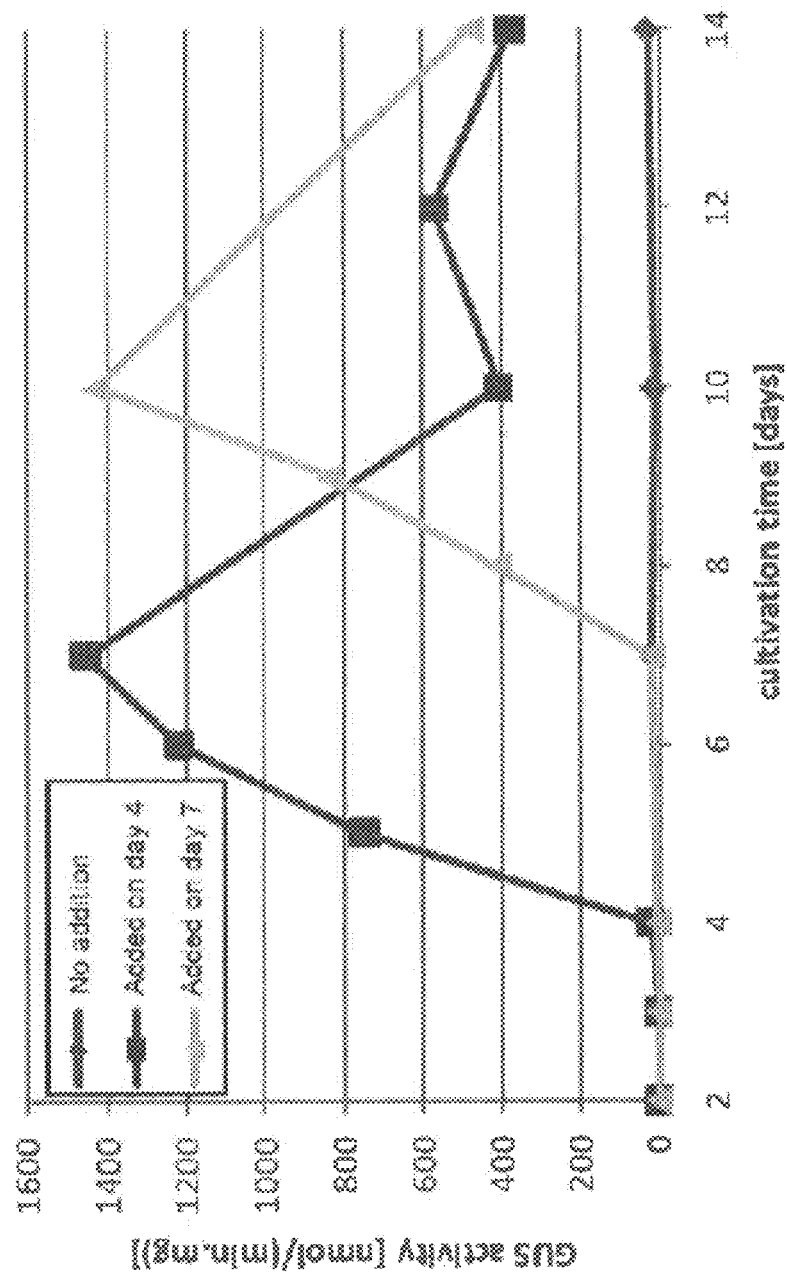
FIG. 3 shows the activity of promoter GAL10-2p. This figure shows the promoter activity induced upon addition of galactose.
Figure 4:
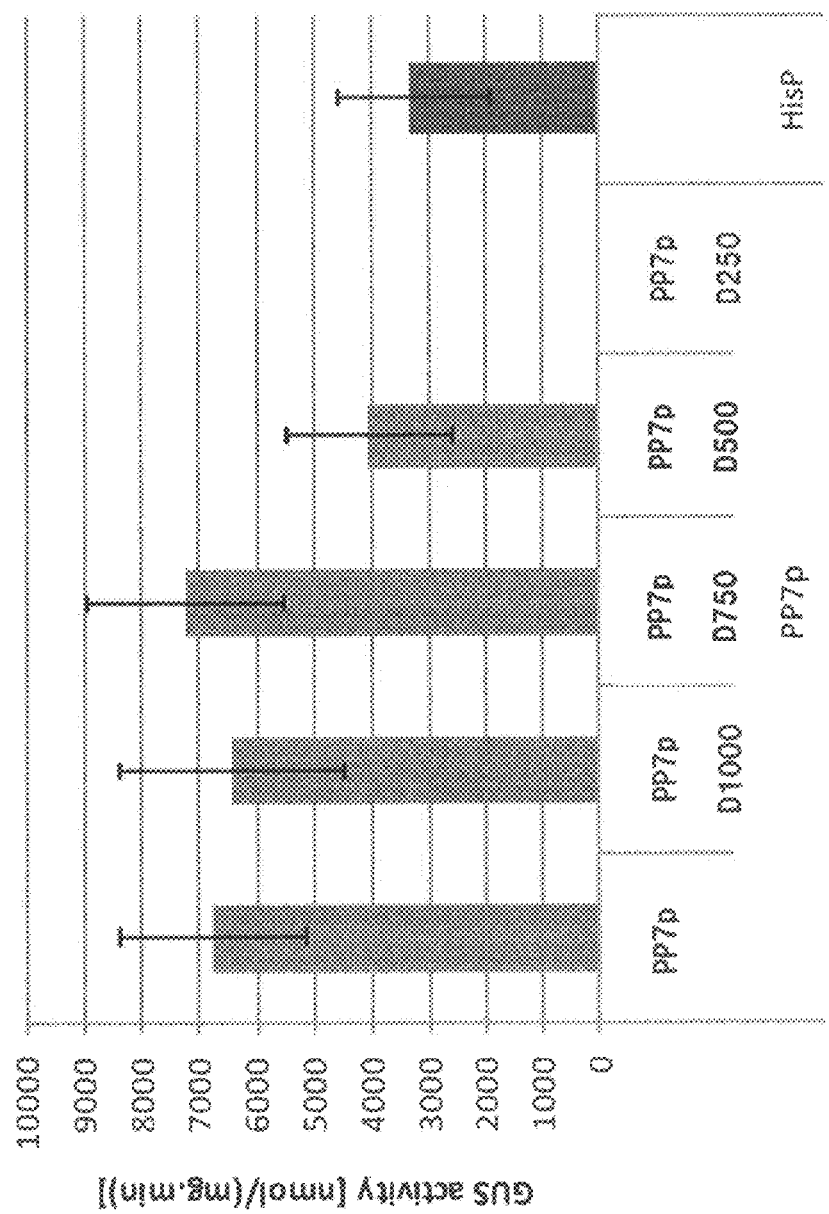
FIG. 4 shows the activity of promoter PP7p and truncated promoters thereof. Culture was conducted in GY medium (10 ml) at 28° C. at 300 rpm for 5 days.
Figure 5:
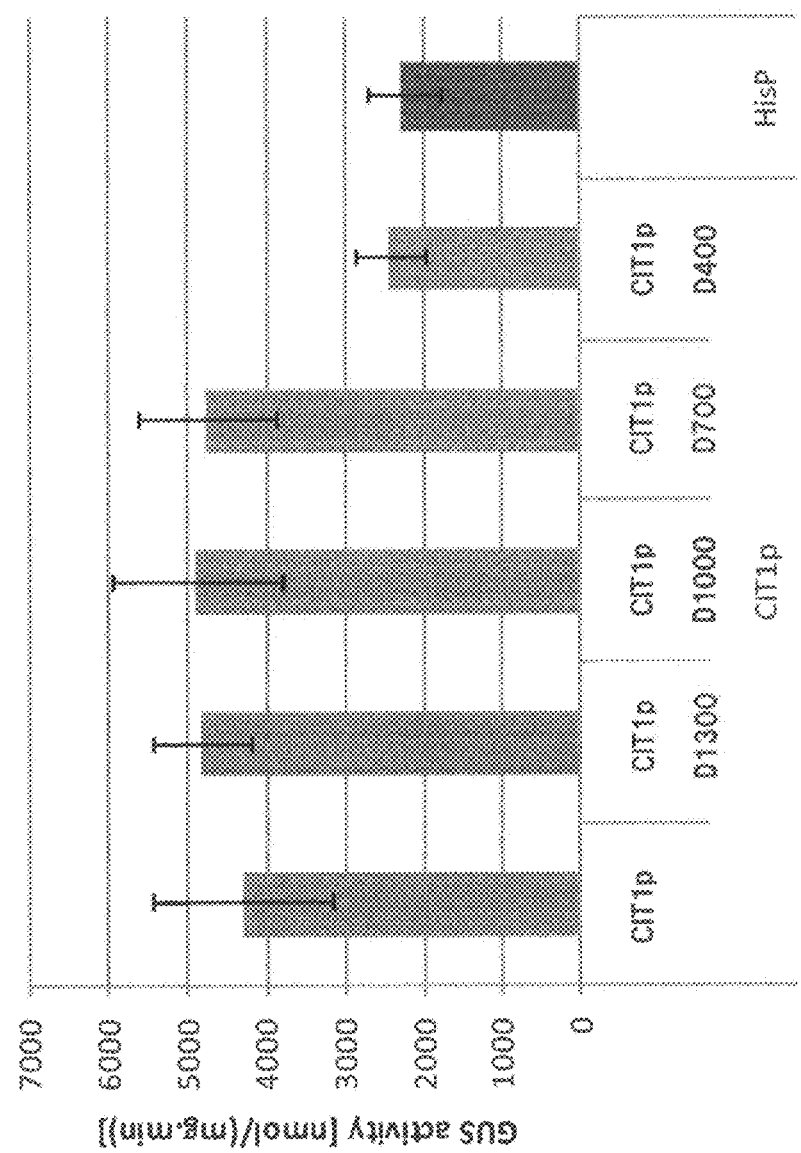
FIG. 5 shows the activity of promoter CIT1p and truncated promoters thereof. Culture was conducted in GY medium (10 ml) at 28° C. at 300 rpm for 3 days.
Figure 6:
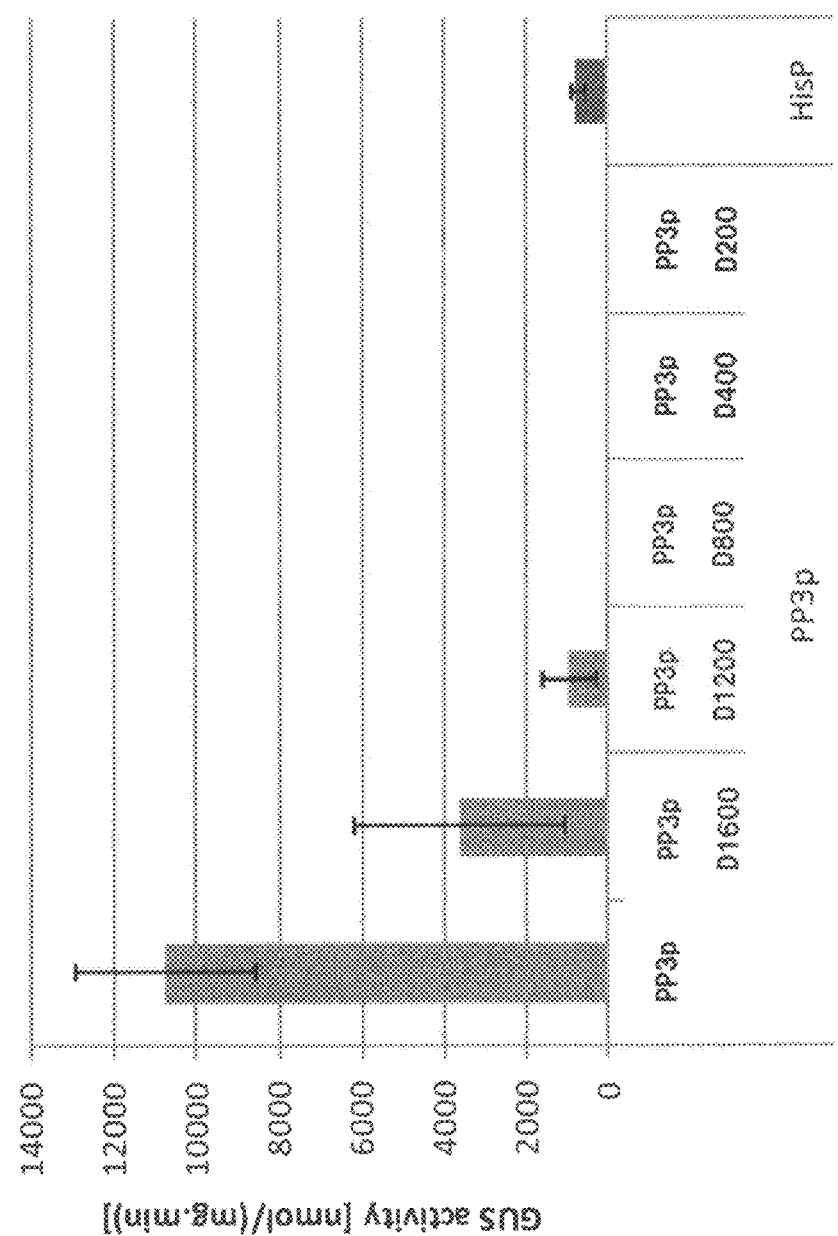
FIG. 6 shows the activity of promoter PP3p and truncated promoters thereof. Culture was conducted in GY medium (10 ml) at 28° C. at 300 rpm for 10 days.
Figure 7:
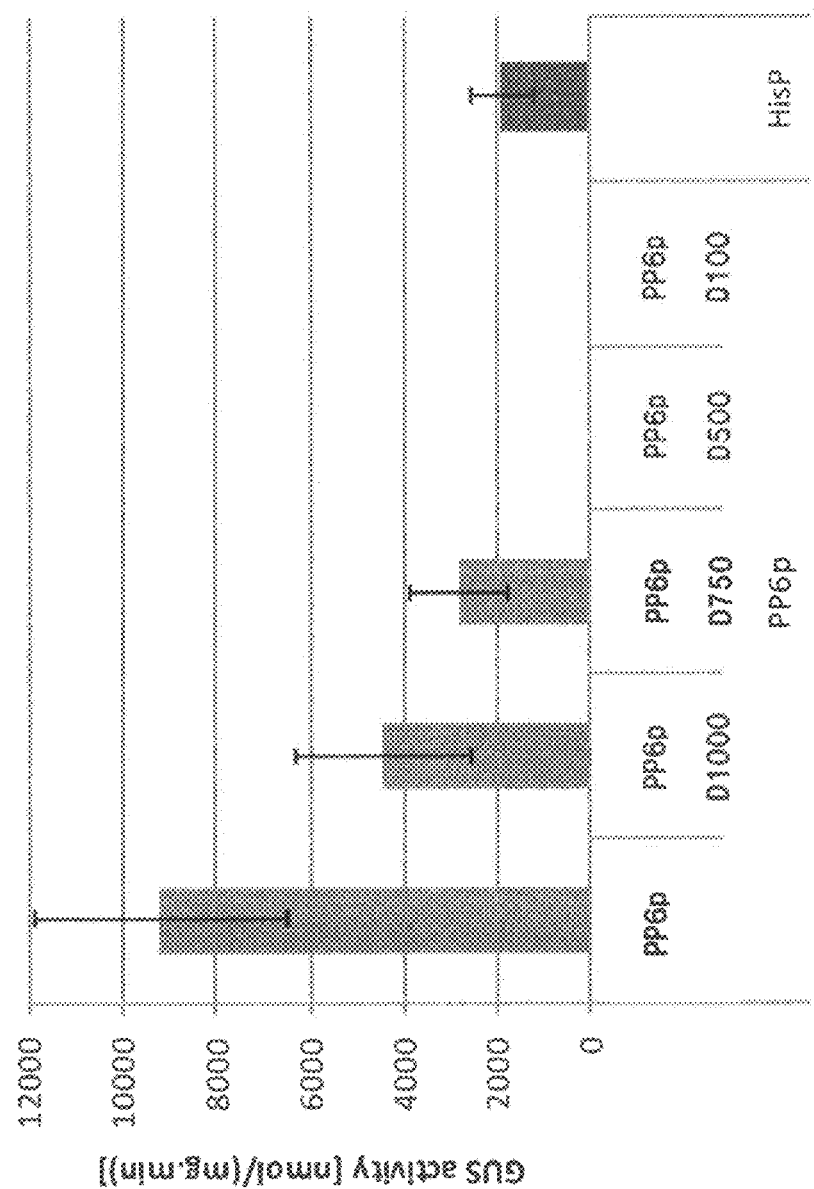
FIG. 7 shows the activity of promoter PP6p and truncated promoters thereof. Culture was conducted in GY medium (10 ml) at 28° C. at 300 rpm for 5 days.
Figure 8:
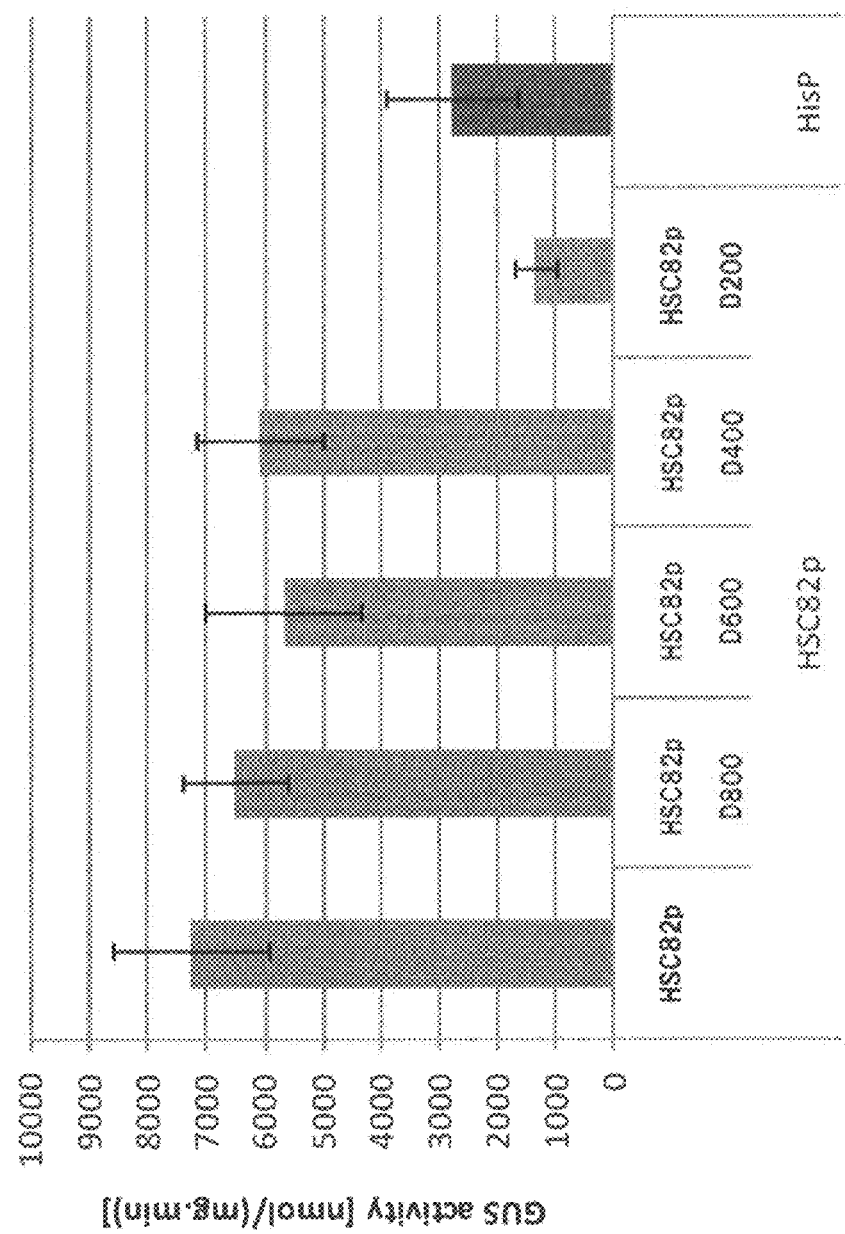
FIG. 8 shows the activity of promoter HSC82p and truncated promoters thereof. Culture was conducted in GY medium (10 ml) at 28° C. at 300 rpm for 5 days.
Figure 9:
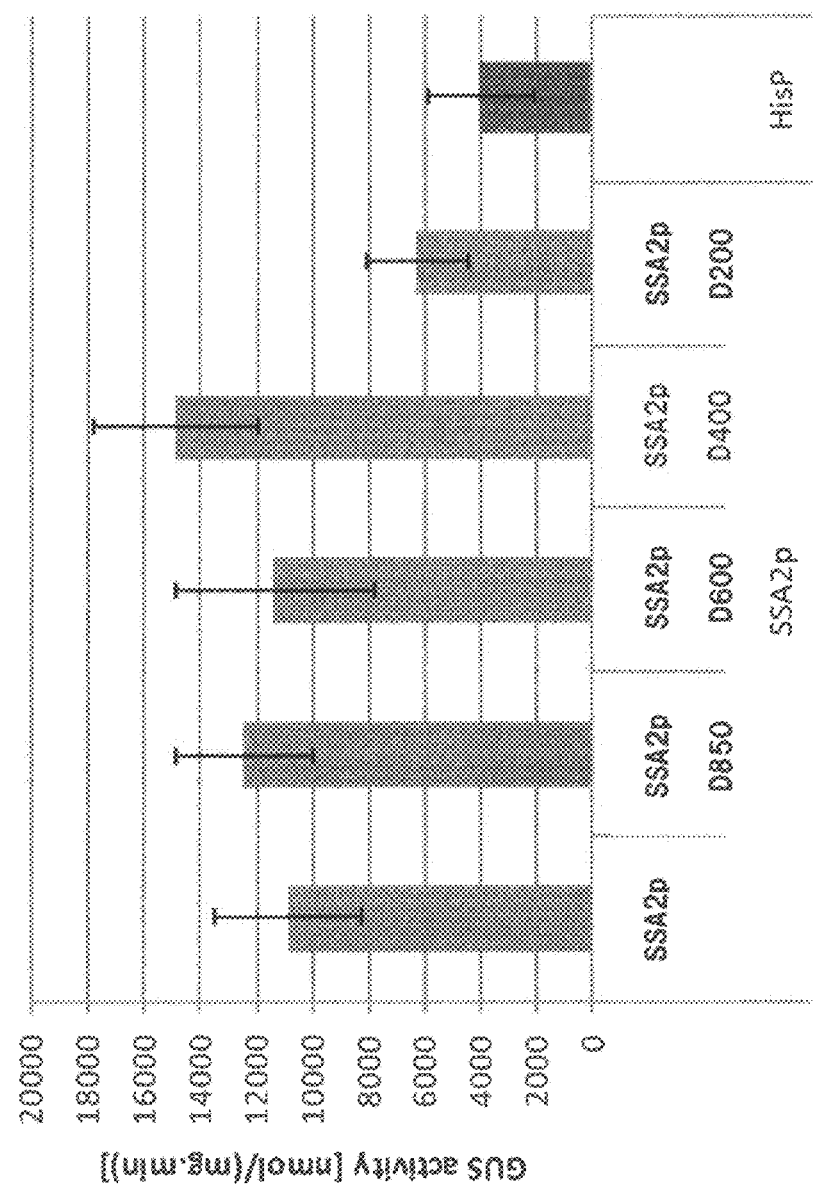
FIG. 9 shows the activity of promoter SSA2p and truncated promoters thereof. Culture was conducted in GY medium (10 ml) at 28° C. at 300 rpm for 5 days.
Figure 10:
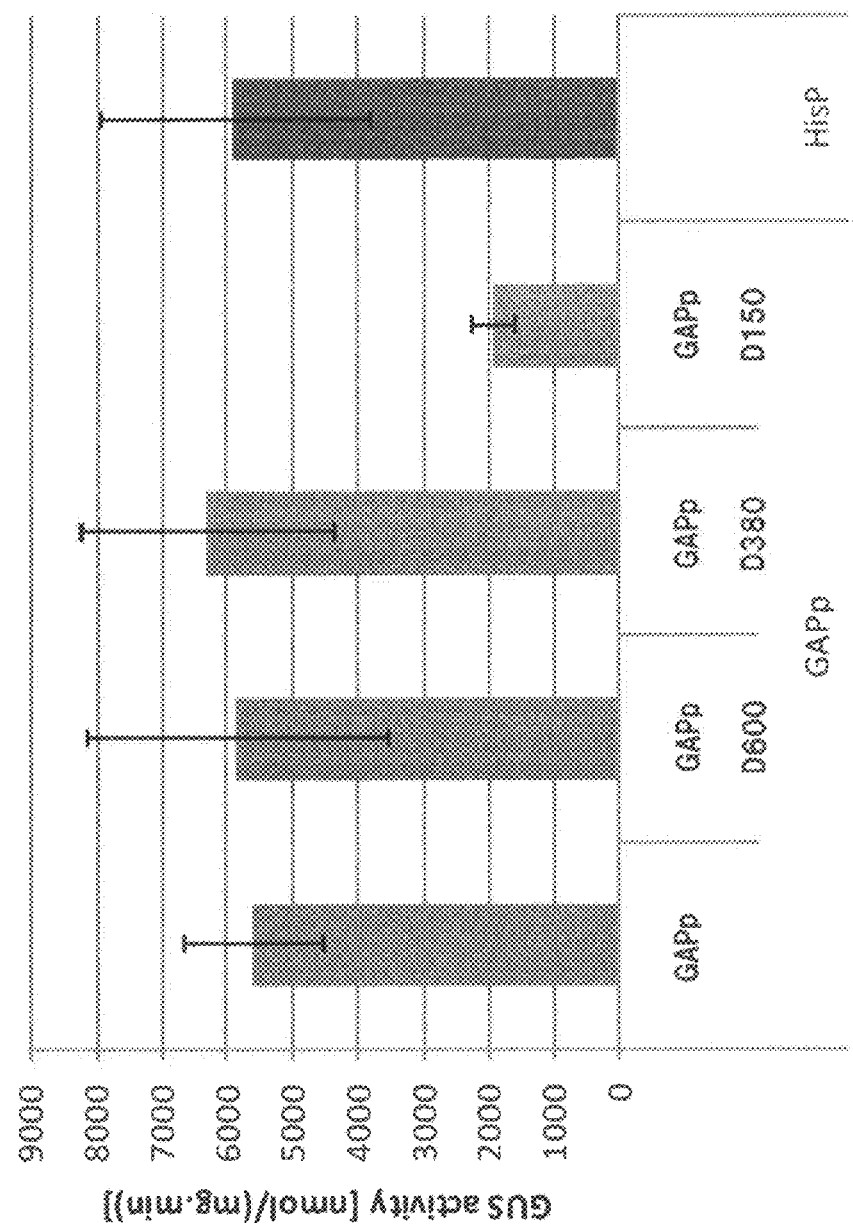
FIG. 10 shows the activity of promoter GAPp and truncated promoters thereof. Culture was conducted in GY medium (10 ml) at 28° C. at 300 rpm for 5 days.

First, stable transformed strains (30 strains) were cultured at 28° C. for 3 days on SC+gal agar medium (SC agar medium containing 2% galactose instead of 2% glucose) and measured for their GUS activity as described above to thereby select 10 strains showing moderate GUS activity. These strains were inoculated into GY liquid medium, and galactose was added thereto at a concentration of 2% on day 4 or 7. Culture conditions were set to 28° C. and 300 rpm. FIG. 3 shows GUS activity measured between 2 and 14 days after initiation of the culture. The promoter GAL10-2p was induced to be expressed upon addition of galactose.

Study on Regions Required for Promoter Activity

To determine a region required for the promoter activity of each promoter, DNA fragments were prepared for each promoter by shortening the upstream region of the promoter, and evaluated for their promoter activity.

To obtain such DNA fragments, the following primers were prepared for each promoter. It should be noted that the underlined parts each represent a restriction enzyme recognition site.

```
PP7p
Primer for amplification of promoter PP7p-D1000
PP7p D1000 F XbaI
                                       (SEQ ID NO: 49)
AGCATCTAGAAAAACTATTCAATAATGGGCG Primer for amplification of promoter PP7p-D750
PP7p D750 F XbaI.
                                       (SEQ ID NO: 50)
ATTTCTAGAATGGCGAGACGCAGGGGGTAG Primer for amplification of promoter PP7p-D500
PP7p D500 F XbaI
                                       (SEQ ID NO: 51)
AATATCTAGAGAGTGGGCACTGAACTAAAAAG Primer for amplification of promoter PP7p-D250
PP7p D250 F XbaI
                                       (SEQ ID NO: 52)
AATATCTAGAGACACTGCATGACGCGAAATC CIT1p
Primer for amplification of promoter CIT1p-D1300
CiT1p D1300 F XbaI
                                       (SEQ ID NO: 53)
AAGTCTAGATGTCAATCATCTTTGCTGCTG Primer for amplification of promoter CIT1p-D1000
CIT1p D1000 F XbaI
                                       (SEQ ID NO: 54)
TGCGTCTAGAATTATAATTATAATGAGGAAGTG Primer for amplification of promoter CIT1p-D700
CIT1p D700 F XbaI
                                       (SEQ ID NO: 55)
TTATCTAGAGGCGAGTGGCGGACTGC
```

-continued

Primer for amplification of promoter CIT1p-D400
CIT1p D400 F XbaI
(SEQ ID NO: 56)
TTGTCTAGACAATTGGCAAGGCTGGGTTG PP3p
Primer for amplification of promoter PP3p-D1600
PP3p D1600 R XbaI
(SEQ ID NO: 57)
AATATCTAGAGATCCTGGTCGAAAAAGACAG Primer for amplification of promoter PP3p-D1200
PP3p D1200 R XbaI
(SEQ ID NO: 58)
AATGTCTAGATGAGTTTCTGTTTTTTCCTTTTTGC Primer for amplification of promoter PP3p-D800
PP3p D800 R XbaI
(SEQ ID NO: 59)
AATATCTAGATGAACAATTCATGCAGCTTCACG Primer for amplification of promoter PP3p-D400
PP3p D400 R XbaI
(SEQ ID NO: 60)
AATATCTAGACGTCTAAGCGTTTACGTGCC Primer for amplification of promoter PP3p-D200
PP3p D200 R XbaI
(SEQ ID NO: 61)
AATATCTAGACTCGTTTTGATGGAGTTCTC PP2p
Primer for amplification of promoter PP2p-D1200
PP2p D1200 F XbaI
(SEQ ID NO: 62)
ATTTCTAGATGCATTTACAGGTGAATATTAC Primer for amplification of promoter PP2p-D800
PP2p D800 F XbaI
(SEQ ID NO: 63)
TTATCTAGACATAAAAGTGTCTGGAGCG Primer for amplification of promoter PP2p-D400
PP2p D400 F XbaI
(SEQ ID NO: 64)
TTATCTAGAACTAAGTGGTGTCTACTTTGG Primer for amplification of promoter PP2p-D200
PP2p D200 F XbaI
(SEQ ID NO: 65)
AATTCTAGAGGATACTCCATCCCCACCC Primer for amplification of promoter PP6ps
PP6ps-D1000
PP6ps D1000 F XbaI
(SEQ ID NO: 66)
AATTCTAGACAGTTACCGTGCGCCCACTG Primer for amplification of promoter PP6ps-D750
PP6ps D750 F XbaI
(SEQ ID NO: 67)
AATTCTAGACTTTCACAAATAGGCATCCTATC Primer for amplification of promoter PP6ps-D500
PP6ps D500 F XbaI
(SEQ ID NO: 68)
AATTCTAGAGGCTTTTTCGTTTATTGGATTG Primer for amplification of promoter PP6ps-D100
PP6ps D100 F XbaI
(SEQ ID NO: 69)
ACGTCTAGATATCCAATTCTCACCACTTC HSC82p
Primer for amplification of promoter HSC82p-D800
HSC82p D800 F XbaI
(SEQ ID NO: 70)
AATTCTAGATTTTACTACCGCATTCCCTTTTC Primer for amplification of promoter HSC82p-D600
HSC82p D600 F XbaI
(SEQ ID NO: 71)
ACGTCTAGACCTTTTCAGTAAACAATTTC Primer for amplification of promoter HSC82p-D400
HSC82p D400 F XbaI
(SEQ ID NO: 72)
ATTTCTAGACACAAAGAAGAAGGGTGTGTC Primer for amplification of promoter HSC82p-D200
HSC82p D200 F XbaI
(SEQ ID NO: 73)
ACGTCTAGAACTGTTTTCTTGAAACTTC SSA2p
Primer for amplification of promoter SSA2p-D850
SSA2p D850 P SpeI
(SEQ ID NO: 74)
AGTAACTAGTTGACGGCGTGTATATGTCAG Primer for amplification of promoter SSA2p-D600
SSA2p D600 F SpeI
(SEQ ID NO: 75)
AGGTACTAGTCCATTGTATCGATTTCTGAT Primer for amplification of promoter SSA2p-D400
SSA2p D400 F SpeI
(SEQ ID NO: 76)
AGTAACTAGTGCTATGCGAACGGTTCATTTTG Primer for amplification of promoter SSA2p-D200
SSA2p D200 F SpeI
(SEQ ID NO: 77)
AGGTACTAGTTTTTTTCTCTCTGGTGTGAACG GAL10-2p
Primer for amplification of promoter GAL10-2p-D2000
GAL10-2p D2000 F XbaI
(SEQ ID NO: 78)
AATTCTAGACGCAGAGTGATGGTCATTACC Primer for amplification of promoter GAL10-2p-D1600
GAL10-2p D1600 F XbaI
(SEQ ID NO: 79)
AATTCTAGACTCTATGGCAAGATTACGAG Primer for amplification of promoter GAL10-2p-D1200
GAL10-2p D1200 F XbaI
(SEQ ID NO: 80)
AATTCTAGATGCTCGTGAAGAGGGGCAC Primer for amplification of promoter GAL10-2p D800
GAL10-2p D800 F XbaI
(SEQ ID NO: 81)
ACGTCTAGACATTTTTTGCCGCCAATTCTG Primer for amplification of promoter GAL10-2p-D400
GAL10-2p D400 F XbaI
(SEQ ID NO: 82)
ATTTCTAGACCCCCGCCTATTTTTTTTTC To prepare truncated promoters of each promoter, the previously prepared vector for evaluation of each promoter was used as a template in PCR with the above primers and the reverse primers used in the examples (PP7p R SpeI, CIT1p R SpeI, PP3p R SpeI, PP2p R SpeI, PP6ps R SpeI, HSC82p R SpeI, SSA2p R SpeI, GAL10-2p R XbaI), each corresponding to the 3'-side of each promoter. The resulting DNA fragments were each excised with restriction enzymes XbaI and SpeI or with a restriction enzyme XbaI and then inserted into the vector for promoter evaluation.

In the same manner as described in the section "Transformation of *Mortierella alpina*," *M. alpina* was transformed to select stable transformed strains. These strains were measured for their GUS activity in the same manner as used in the examples. It should be noted that the number of days for culture was set to 3 days (CIT1p), 5 days (PP7p, PP6p, HSC82p, SSA2p, GAPp) or 10 days (PP3p), depending on the properties of each promoter. The results obtained are shown in FIGS. 4 to 10.

Figure 11:
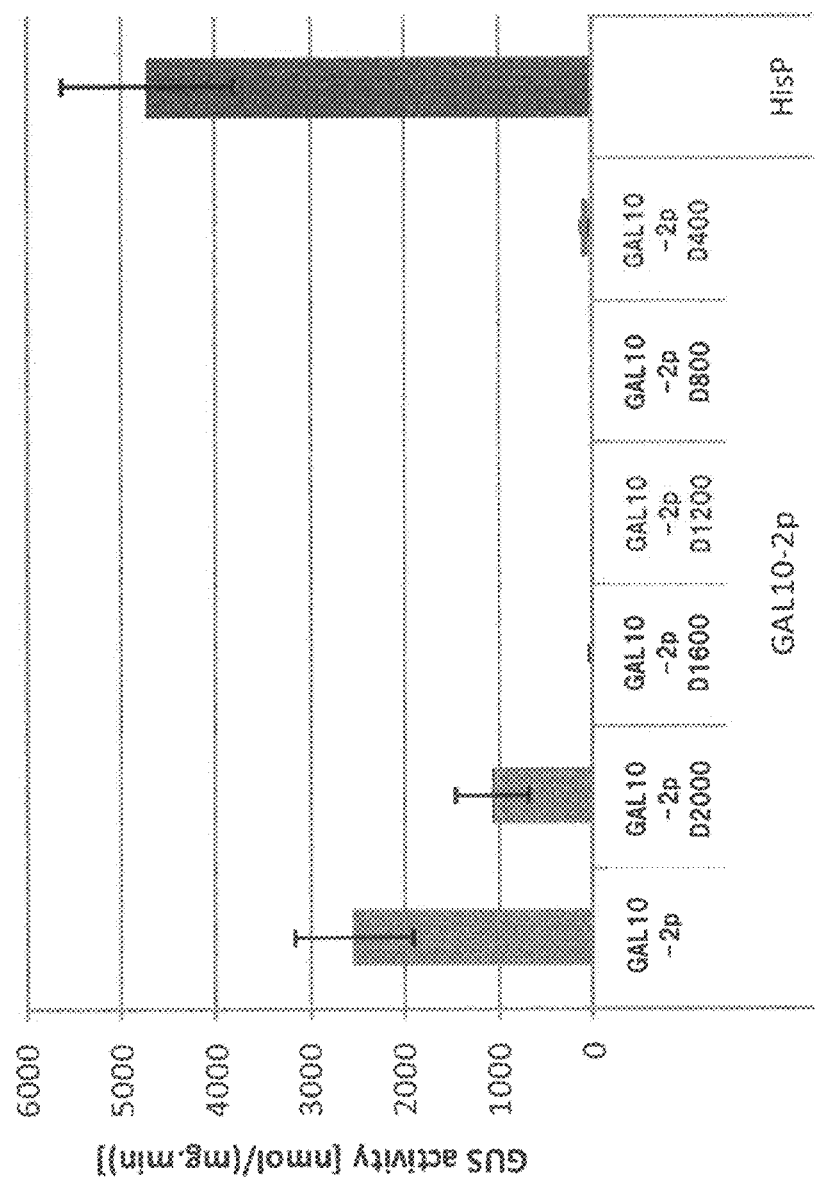
FIG. 11 shows the activity of promoter GAL10-2p and truncated promoters thereof.

In the case of the galactose-inducible promoter, stable transformed strains were pre-cultured at 28° C. for 3 days on SC+gal agar medium (SC agar medium containing 2% galactose instead of 2% glucose) or pre-cultured at 28° C. at 300 rpm for 4 days in SC+raf medium (SC liquid medium containing 2% raffinose instead of 2% glucose), followed by addition of galactose to give a final concentration of 2%. Culture was continued for an additional 1 day, and the cells were measured for their GUS activity. The results obtained are shown in FIG. 11.

As can be seen from FIGS. 4 to 11, the full-length promoters and truncated promoters shown in Table I above were each confirmed to show GUS protein activity of 500 nmol/(mg·min) or higher.

INDUSTRIAL APPLICABILITY

The present invention enables the high expression of target genes in lipid-producing fungi and thereby allows efficient synthesis and collection of target proteins, lipids and fatty acids.

Sequence Listing Free Text

SEQ ID NOs: 31 to 82: synthetic DNAs

Sequence Listing

We claim:

1. A vector comprising a polynucleotide selected from:
   (a) a polynucleotide which contains any one nucleotide sequence selected from SEQ ID NO: 17, SEQ ID NO: 18, SEQ ID NO: 19, SEQ ID NO: 20 and SEQ ID NO: 21; or
   (b) a polynucleotide which has a nucleotide sequence sharing an identity of 90% or more with any one nucleotide sequence selected from SEQ ID NO: 17, SEQ ID NO: 18, SEQ ID NO: 19, SEQ ID NO: 20 and SEQ ID NO: 21 and which shows promoter activity in cells of microorganisms belonging to the genus *Mortierella*.

2. The vector according to claim 1, wherein the promoter activity is confirmed as β-D-glucuronidase (GUS) protein activity of at least 500 nmol/(mg·min) upon expression of GUS reporter gene in cells of microorganisms belonging to the genus *Mortierella*.

3. The vector according to claim 1, which comprises any one nucleotide sequence selected from SEQ ID NO: 17, SEQ ID NO: 18, SEQ ID NO: 19, SEQ ID NO: 20 and SEQ ID NO: 21.

4. The vector according to claim 1, which is DNA.

5. A microbial transformant transformed with the vector according to claim 1.

6. The transformant according to claim 5, wherein the transformant is a lipid-producing fungus.

7. The transformant according to claim 6, wherein the lipid-producing fungus is *Mortierella alpina*.

* * * * *

SEQUENCE LISTING

```
<160> NUMBER OF SEQ ID NOS: 82

<210> SEQ ID NO 1
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
tgaccgtgcg cttttttgaga cggttgatag gtacaacacg acgctaacat gaggctagtg      60
cggcaacttt tttacgccct cggtaacaaa aaaatcgtct cattcatatg tcagaatcgt     120
gctctctttg tcaccaagga gacgcctctc cctcccgtca gggccttgtc aaaactaccg     180
cccaaaacac aaagttggca tccgatgaaa gtcgagtgag cgtctatttt ttttatttta     240
gatcgcttct aatgcagatc tgaaaactat tcaataatgg gcgcccactc aaacacgcgg     300
ccagggcgga aaaggagtg ggagttgtga aaaatgagag acaattgttg attctttggg      360
atactgatgt ccatttggtg ctgctcgtcc tcctttgggt caaaagaagg cgcagccatg     420
cacggccctt tcttattgac aaagtcccta actgcttacc aaagtctttt ctagctcttc     480 atctttttatt ttttataaaa aaaggtccga caccccctatg ttcgaaggtg ctagacggat    540
caagaatatc atcgagatgg cgagacgcag ggggtagagc ggacatagtg acagtttcaa    600
ggtcagcata tagaaaggcg gtcaaggcaa gctggtgcct gagatccgtt tgccagacaa     660
agagaagatg ttcgtgtatg gtcacgatcc cgaaaagaat aattcaaaac agctctaggt    720
gaaggctata ttcgtcctca gatctttcta cacagaaagg gaggtacact tgggccactt    780
gatgcaactt tctccgacgt tgactgggtc tgaaaaacaa agaacctcag tttcggtccg    840
agagtgggca ctgaactaaa aaggaaaccc attttcgagg cattcggtcg ggttagagtt    900
caattcttat tttatggtcc tcccgtcgga tgtgtcagtg tttgggcggc caagacgaca    960
acagtgaggg gatcgagcac acctgctgag ggggcggtg tgctctcaaa tagggaaaat    1020
atccaatcta ggccgttccc ttattgaccg atagttttc tttcctttgt ttgctgactg    1080
agtttcgggt agacactgca tgacgcgaaa tccatcgaag gagtttgaaa atatcgacgt    1140
ggaggcaaaa tgcttacctc cccaatactc gcaatgctgc cccatgactt tgcgcgtgca    1200
acagaaccga aaaaaggtat aagaacctgg tttccgtcct ccaccatttg tctttttctct    1260 cttctaacct tcattccaat ctacaacaca agaacaaccc acaaataacc caactcaatc    1320 ccaccttttca acaaatatac g                                              1341
```

<210> SEQ ID NO 2
<211> LENGTH: 1079
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| | | | | | |
|---|---|---|---|---|---|
| aaaactattc | aataatgggc | gcccactcaa | acacgcggcc | agggcggaaa | aaggagtggg | 60 |
| agttgtgaaa | aatgagagac | aattgttgat | tctttgggat | actgatgtcc | atttggtgct | 120 |
| gctcgtcctc | ctttgggtca | aagaaggcg | cagccatgca | cggcccttc | ttattgacaa | 180 |
| agtccctaac | tgcttaccaa | agtctttct | agctcttcat | cttttatttt | ttataaaaaa | 240 |
| aggtccgaca | cccctatgtt | cgaaggtgct | agacggatca | agaatatcat | cgagatggcg | 300 |
| agacgcaggg | ggtagagcgg | acatagtgac | agtttcaagg | tcagcatata | gaaaggcggt | 360 |
| caaggcaagc | tggtgcctga | gatccgtttg | ccagacaaag | agaagatgtt | cgtgtatggt | 420 |
| cacgatcccg | aaaagaataa | ttcaaaacag | ctctaggtga | aggctatatt | cgtcctcaga | 480 |
| tctttctaca | cagaaaggga | ggtacacttg | ggccacttga | tgcaactttc | tccgacgttg | 540 |
| actgggtctg | aaaaacaaag | aacctcagtt | tcggtccgag | agtgggcact | gaactaaaaa | 600 |
| ggaaacccat | tttcgaggca | ttcggtcggg | ttagagttca | attcttattt | tatggtcctc | 660 |
| ccgtcggatg | tgtcagtgtt | tgggcggcca | agacgacaac | agtgagggga | tcgagcacac | 720 |
| ctgctgaggg | gggcggtgtg | ctctcaaata | gggaaaatat | ccaatctagg | ccgttccctt | 780 |
| attgaccgga | tagttttctt | tcctttgttt | gctgactgag | tttcgggtag | acactgcatg | 840 |
| acgcgaaatc | catcgaagga | gtttgaaaat | atcgacgtgg | aggcaaaatg | cttacctccc | 900 |
| caatactcgc | aatgctgccc | catgactttg | cgcgtgcaac | agaaccgaaa | aaggtataa | 960 |
| gaacctggtt | tccgtcctcc | accatttgtc | ttttctctct | tctaaccttc | attccaatct | 1020 |
| acaacacaag | aacaacccac | aaataaccca | actcaatccc | acctttcaac | aaatatacg | 1079 |

<210> SEQ ID NO 3
<211> LENGTH: 785
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| | | | | | |
|---|---|---|---|---|---|
| atggcgagac | gcaggggta | gagcggacat | agtgacagtt | tcaaggtcag | catatagaaa | 60 |
| ggcggtcaag | gcaagctggt | gcctgagatc | cgtttgccag | acaaagagaa | gatgttcgtg | 120 |
| tatggtcacg | atcccgaaaa | gaataattca | aaacagctct | aggtgaaggc | tatattcgtc | 180 |
| ctcagatctt | tctacacaga | aagggaggta | cacttgggcc | acttgatgca | actttctccg | 240 |
| acgttgactg | ggtctgaaaa | acaaagaacc | tcagtttcgg | tccgagagtg | gcactgaac | 300 |
| taaaaaggaa | acccattttc | gaggcattcg | gtcgggttag | agttcaattc | ttattttatg | 360 |
| gtcctcccgt | cggatgtgtc | agtgtttggg | cggccaagac | gacaacagtg | aggggatcga | 420 |
| gcacacctgc | tgagggggc | ggtgtgctct | caaatagggga | aaatatccaa | tctaggccgt | 480 |
| tcccttattg | accggatagt | tttctttcct | ttgtttgctg | actgagtttc | gggtagacac | 540 |
| tgcatgacgc | gaaatccatc | gaaggagttt | gaaaatatcg | acgtggaggc | aaaatgctta | 600 |
| cctccccaat | actcgcaatg | ctgccccatg | actttgcgcg | tgcaacagaa | ccgaaaaaag | 660 |

```
gtataagaac ctggttttccg tcctccacca tttgtctttt ctctcttcta accttcattc    720
caatctacaa cacaagaaca acccacaaat aacccaactc aatcccacct ttcaacaaat    780
atacg                                                                785
```

```
<210> SEQ ID NO 4
<211> LENGTH: 500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gagtgggcac tgaactaaaa aggaaaccca ttttcgaggc attcggtcgg gttagagttc     60
aattcttatt ttatggtcct cccgtcggat gtgtcagtgt ttgggcggcc aagacgacaa    120
cagtgagggg atcgagcaca cctgctgagg ggggcggtgt gctctcaaat agggaaaata    180
tccaatctag gccgttccct tattgaccgg atagttttct ttcctttgtt tgctgactga    240
gtttcgggta gacactgcat gacgcgaaat ccatcgaagg agtttgaaaa tatcgacgtg    300
gaggcaaaat gcttacctcc ccaatactcg caatgctgcc ccatgacttt gcgcgtgcaa    360
cagaaccgaa aaaggtata agaacctggt ttccgtcctc caccatttgt cttttctctc    420
ttctaacctt cattccaatc tacaacacaa gaacaaccca caataaccca aactcaatcc    480
cacctttcaa caaatatacg                                                500
```

```
<210> SEQ ID NO 5
<211> LENGTH: 1593
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
attttctaga cacctcaaaa acgtgccttg ttgttcctgt taggctgaag ctctgctgta     60
cacacgaggt tgaagccggg taggttttag ttgggtgcga gtgccgtgat ctgggccgag    120
agtttgtcac tgaatcagct aaatagcgga aagtgtgatg cacaatcagg aacgttggtg    180
gcacgatgca acgtcgaggt atgggcggcc gtgctcgctg gtgcttcctt taagatcgag    240
gacatagtgc agtacgtctt tcttgagctg aagtttgtgt gtctcgtctc tctctttctc    300
tctcgcatcc tgttaatgtg tcgtccaaag tgtcaatcat ctttgctgct gatctctggg    360
cactttcttc cttagtgtgc cgtatatgga caattgtggg gttccctgct cttaaggcaa    420
gggcagatag cgtgggtagg ttggaaactc aagcgaaata acacagtgaa gccacgcttg    480
atgagaggaa acatgttgca caaaagtgta aaaaaaaaaa ttagagactg ccagagggag    540
gtgaggcaag ttgtgacaaa tcctatttta tgtattgtca agcctgaggt cgacggccat    600
cctttactcg cttcagcttt cggatcacat attataatta taatgaggaa gtgttggttt    660
gggagacagg agtggaggtt ttgataaata aaaaaagtgg cagatcaagg agaatgtggc    720
gatccatgaa caaaaaagat ggcggttttt tcttgatcga attcggtctc ccaccagatc    780
atatgccgat ggtagagttg atctgccggt ggttatacca cggacctggt ggtgtataga    840
ttatcaagct catttccaag tgcagcgtag aatacaaaga cgctagatga tccaagcgac    900
gatgggtacg gcgatgatga tgccaacgat ggcgagtggc ggactgctcc gtcccgagcg    960
```

```
ggatgatgat tgtgccgatg tggaaaccac ctgcgacggt ggtctacaat actgttgctg    1020
ttataaataa cggcgttaga gtactactat agtgtagact gatgggttct ctgtgaaagg    1080
aaagaggagt cggtattttg aatactagcc cgagggggtt tttttgatgg gttgtgcctg    1140
aatagttgtt gcgctgttct ttttgatct aaagagttga ggagcagccc gtacgtcact     1200
ttatcgattc aatcgccggt ggcctgtatt caattggcaa ggctgggttg ctgcccggtg    1260
cttatctcca gaggacaggg cctggcgagg aaggggagat gctcagactg ctcagacagg    1320
cacacagaca atttcaaagt ccacatgcaa agaaaacaaa aaaaaaaaa aatgtaattc     1380 ccttccccct gcaacatgtc gtatgtgcgg gtggaaggaa acgtttctgt tctcatcaca    1440
tccgatcaca agtgtctctg tctccgcccg acgctttttt ttattcttct tttttctgt    1500 cttttctctt ttcttttttc tcttctcttt tctttcttct ttctctcctc atcttcttcc    1560
actcactccc ctctctccat acacatatcc gcc                                  1593

<210> SEQ ID NO 6
<211> LENGTH: 1263
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
tgtcaatcat ctttgctgct gatctctggg cactttcttc cttagtgtgc cgtatatgga      60
caattgtggg gttccctgct cttaaggcaa gggcagatag cgtgggtagg ttggaaactc     120
aagcgaaata acacagtgaa gccacgcttg atgagaggaa acatgttgca caaaagtgta    180
aaaaaaaaaa ttagagactg ccagaggag gtgaggcaag ttgtgacaaa tcctattta      240 tgtattgtca agcctgaggt cgacggccat cctttactcg cttcagcttt cggatcacat    300
attataatta taatgaggaa gtgttggttt gggagacagg agtggaggtt ttgataaata    360
aaaaaagtgg cagatcaagg agaatgtggc gatccatgaa caaaaaagat ggcggttttt    420
tcttgatcga attcggtctc ccaccagatc atatgccgat ggtagagttg atctgccggt    480
ggttatacca cggacctggt ggtgtataga ttatcaagct catttccaag tgcagcgtag    540
aatacaaaga cgctagatga tccaagcgac gatgggtacg gcgatgatga tgccaacgat    600
ggcgagtggc ggactgctcc gtcccgagcg ggatgatgat tgtgccgatg tggaaaccac    660
ctgcgacggt ggtctacaat actgttgctg ttataaataa cggcgttaga gtactactat    720
agtgtagact gatgggttct ctgtgaaagg aaagaggagt cggtattttg aatactagcc    780
cgagggggtt tttttgatgg gttgtgcctg aatagttgtt gcgctgttct ttttgatct     840 aaagagttga ggagcagccc gtacgtcact ttatcgattc aatcgccggt ggcctgtatt    900
caattggcaa ggctgggttg ctgcccggtg cttatctcca gaggacaggg cctggcgagg    960
aaggggagat gctcagactg ctcagacagg cacacagaca atttcaaagt ccacatgcaa    1020
agaaaacaaa aaaaaaaaa aatgtaattc ccttccccct gcaacatgtc gtatgtgcgg    1080
gtggaaggaa acgtttctgt tctcatcaca tccgatcaca agtgtctctg tctccgcccg    1140
acgctttttt ttattcttct tttttctgt cttttctctt ttcttttttc tcttctcttt    1200
tctttcttct ttctctcctc atcttcttcc actcactccc ctctctccat acacatatcc    1260
gcc                                                                   1263

<210> SEQ ID NO 7
```

```
<211> LENGTH: 963
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
attataatta taatgaggaa gtgttggttt gggagacagg agtggaggtt ttgataaata      60
aaaaaagtgg cagatcaagg agaatgtggc gatccatgaa caaaaaagat ggcggttttt     120
tcttgatcga attcggtctc ccaccagatc atatgccgat ggtagagttg atctgccggt     180
ggttatacca cggacctggt ggtgtataga ttatcaagct catttccaag tgcagcgtag     240
aatacaaaga cgctagatga tccaagcgac gatgggtacg gcgatgatga tgccaacgat     300
ggcgagtggc ggactgctcc gtcccgagcg ggatgatgat tgtgccgatg tggaaaccac     360
ctgcgacggt ggtctacaat actgttgctg ttataaataa cggcgttaga gtactactat     420
agtgtagact gatgggttct ctgtgaaagg aaagaggagt cggtattttg aatactagcc     480
cgagggggtt ttttttgatgg gttgtgcctg aatagttgtt gcgctgttct ttttttgatct     540 aaagagttga ggagcagccc gtacgtcact ttatcgattc aatcgccggt ggcctgtatt     600
caattggcaa ggctggggttg ctcccggtg cttatctcca gaggacaggg cctggcgagg     660
aaggggagat gctcagactg ctcagacagg cacacagaca atttcaaagt ccacatgcaa     720
agaaaacaaa aaaaaaaaaa aatgtaattc ccttcccccct gcaacatgtc gtatgtgcgg     780
gtggaaggaa acgtttctgt tctcatcaca tccgatcaca agtgtctctg tctccgcccg     840 acgcttttttt ttattcttct tttttttctgt cttttctctt ttcttttttttc tcttctcttt     900 tctttcttct ttctctcctc atcttcttcc actcactccc ctctctccat acacatatcc     960
gcc     963

<210> SEQ ID NO 8
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
ggcgagtggc ggactgctcc gtcccgagcg ggatgatgat tgtgccgatg tggaaaccac      60
ctgcgacggt ggtctacaat actgttgctg ttataaataa cggcgttaga gtactactat     120
agtgtagact gatgggttct ctgtgaaagg aaagaggagt cggtattttg aatactagcc     180
cgagggggtt ttttttgatgg gttgtgcctg aatagttgtt gcgctgttct ttttttgatct     240 aaagagttga ggagcagccc gtacgtcact ttatcgattc aatcgccggt ggcctgtatt     300
caattggcaa ggctggggttg ctcccggtg cttatctcca gaggacaggg cctggcgagg     360
aaggggagat gctcagactg ctcagacagg cacacagaca atttcaaagt ccacatgcaa     420
agaaaacaaa aaaaaaaaaa aatgtaattc ccttcccccct gcaacatgtc gtatgtgcgg     480
gtggaaggaa acgtttctgt tctcatcaca tccgatcaca agtgtctctg tctccgcccg     540 acgcttttttt ttattcttct tttttttctgt cttttctctt ttcttttttttc tcttctcttt     600 tctttcttct ttctctcctc atcttcttcc actcactccc ctctctccat acacatatcc     660
gcc     663
```

```
<210> SEQ ID NO 9
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
caattggcaa ggctgggttg ctgcccggtg cttatctcca gaggacaggg cctggcgagg      60 aagggagat gctcagactg ctcagacagg cacacagaca atttcaaagt ccacatgcaa     120
agaaaacaaa aaaaaaaaaa aatgtaattc ccttccccct gcaacatgtc gtatgtgcgg    180
gtggaaggaa acgtttctgt tctcatcaca tccgatcaca agtgtctctg tctccgcccg    240 acgcttttt ttattcttct ttttttctgt cttttctctt ttcttttttc tcttctcttt     300
tctttcttct ttctctcctc atcttcttcc actcactccc ctctctccat acacatatcc    360
gcc                                                                   363

<210> SEQ ID NO 10
<211> LENGTH: 2294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
tcgtgttatc ttgcgctgca tgtttcgttg ccgagtcgtt attaatctat gggcgttcta     60
ctctaggttt tgcgtacgtt accaatgcat ttggacctcc tgagacttta ctgggagact    120
acagggccaa gactttgctg gaccgtgtcg tctatgctag aaaggaggag ctcggattgc    180
tcccaatgaa ggaggccaac agcgaggcca agagtgaggc caagaactaa aggcgttcca    240
ttaaaactat gctgcttttc gtgctcccct tttttttttt ttttttttttt ttacttttac   300 ttttgcctga cgtgaactgc acaatgctgc aaaatcatga aggagtcaag acaatgacgg    360
gagagagtaa acaccatccc caccactctg tagaggaaca tcacgcggtt ccgttttgtg    420
cactcctccc tttgagacaa tccttgcagt ctgatgggcg cttttcttct cacggttgtc    480
gctgaaattt tgttgcctca caggcgcgta tgatatcaat tactgcacgc cgttgcttgg    540
tgttcttggc tatctctttt ccagagctga tgctggtcgg cgtatctcta tgatgcaacc    600
ttccctgcct tctctgattc ctgtagtctg cagcctctag ttcgatcctg gtcgaaaaag    660
acaggcgcaa tgtccctcat cccggaactt tcggcaaagc ccagttcttc gccatcttta    720
aaacaacagc acctacgccc tcctcgcagt actttgatcc ctccccattc aaaagagaca    780
ttttagtaga aaacggttga gaaggaaaaa gatttctgta gaacgtaaag catgagaaaa    840
aagtaatgct ctccctgtag atgcatcctc ctgtttctgg cttactttga accgacttg     900 ctccaaacga tcatgcccaa attaataaag gacatcgacc aacggaggct ttagcaggac    960
agtgcgcctc tatgtacatg tacactacaa ggatgatcat gcattgtatg ccgatttgg   1020 ctgcattgcg atcgcactgg cgagacagag aaagggggtg tgtatttcaa gaacgagaag   1080 gcgaggggg gactgagttt ctgtttttc cttttttgcat aactgtcgac aagagacggt    1140
gtatgaagtg aagaggaaac acaaggggtg catggacgtt gaggaacagt aacattcgtg   1200
atgggtctag gtgattgggg gcagtgtgcc ttctaatgca caccagaacc aagccattga   1260
gtatcgctat ggcttgccta tgatagcatg gaccgcagaa agaaaccttt ttgctgctaa   1320
```

```
ctgggaccag aatagcgcgg tctgtcatca actaacgtta tggtcctctg tagcctggga   1380
agaacggact gagggtgttt cgttgaatgt caagggcat gcgccaaaaa acacatatga   1440
cgggggaaca tgcggaagcg cgattgtgat tttcattctt ttttcggtct gtgtgaacaa   1500
ttcatgcagc ttcacgagca tgttcgatgg aaaggaacag tgctctattt ttcagagtag   1560
tctagcatag gatttgagag ccgagttgct tgcttacgat gtcactgtgt ggagtgttgg   1620
agcgcaatcc ctgcttttc aattatcttt ggcatacgtg gaagacctgg ccgttcagta   1680
cacgcccgcg aaatgtcatt caatgccctg tccaatcttg accataggct tagacacggt   1740
cccccaagct tcctccaaac aatcgcgttt atttatatac ttcatcatgc atatgagatc   1800
acacctgtta aactagatcg caaccgtaca atagtgtgct ctcagttgac caggggcagc   1860
tacaaaacgg tccggctgga gtgttttttt tgacgtctaa gcgtttacgt gccattgact   1920
acttcgagct ttcaaacgct tggcccaggg aggtctcgac agctaagaga acgtacgcga   1980
ccttctcttt ggtccattga gcaaagtttc ccacacacat agtagttgga tatgcctgtt   2040
caccatcgtt gggcattgca ccaaaaggca tcccgctgaa agctgtcatg aaactcgttt   2100
tgatggagtt ctcaatcaca tcacctcaca tcattttgca ccctgcccgg gtggaaaaaa   2160
tactcccagg cctcagctcg cgcctcctca cgatcgcttt tcgtataaaa accatcctcc   2220
ttcgcgctcc ttttcatcca tattctcact tttgtctcta tccctcagc taaaaccaac   2280 acctctaaat catc                                                      2294

<210> SEQ ID NO 11
<211> LENGTH: 1651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gatcctggtc gaaaaagaca ggcgcaatgt ccctcatccc ggaactttcg gcaaagccca    60
gttcttcgcc atctttaaaa caacagcacc tacgccctcc tcgcagtact ttgatccctc   120
cccattcaaa agagacattt tagtagaaaa cggttgagaa ggaaaaagat ttctgtagaa   180
cgtaaagcat gagaaaaaag taatgctctc cctgtagatg catcctcctg tttctggctt   240
tactttgaac cgacttgctc caaacgatca tgcccaaatt aataaaggac atcgaccaac   300
ggaggcttta gcaggacagt gcgcctctat gtacatgtac actacaagga tgatcatgca   360
ttgtatgccg attttggctg cattgcgatc gcactggcga acagagaaa gggggtgtgt   420 atttcaagaa cgagaaggcg agggggggac tgagtttctg ttttttcctt tttgcataac   480
tgtcgacaag agacggtgta tgaagtgaag aggaaacaca aggggtgcat ggacgttgag   540
gaacagtaac attcgtgatg ggtctaggtg attgggggca gtgtgccttc taatgcacac   600
cagaaccaag ccattgagta tcgctatggc ttgcctatga tagcatggac cgcagaaaga   660
aacctttttg ctgctaactg ggaccagaat agcgcggtct gtcatcaact aacgttatgg   720
tcctctgtag cctgggaaga acggactgag ggtgtttcgt tgaatgtcaa ggggcatgcg   780
ccaaaaaaca catgacgg gggaacatgc ggaagcgcga ttgtgatttt cattcttttt   840
tcggtctgtg tgaacaattc atgcagcttc acgagcatgt tcgatggaaa ggaacagtgc   900
tctatttttc agagtagtct agcataggat ttgagagccg agttgcttgc ttacgatgtc   960
actgtgtgga gtgttggagc gcaatccctg cttttcaat tatctttggc atacgtggaa  1020
```

-continued

```
gacctggccg ttcagtacac gcccgcgaaa tgtcattcaa tgccctgtcc aatcttgacc    1080
ataggcttag acacggtccc ccaagcttcc tccaaacaat cgcgtttatt tatatacttc    1140
atcatgcata tgagatcaca cctgttaaac tagatcgcaa ccgtacaata gtgtgctctc    1200
agttgaccag gggcagctac aaaacggtcc ggctggagtg ttttttttga cgtctaagcg    1260
tttacgtgcc attgactact tcgagctttc aaacgcttgg cccagggagg tctcgacagc    1320
taagagaacg tacgcgacct tctctttggt ccattgagca agtttccca cacacatagt     1380 agttggatat gcctgttcac catcgttggg cattgcacca aaaggcatcc cgctgaaagc    1440
tgtcatgaaa ctcgttttga tggagttctc aatcacatca cctcacatca ttttgcaccc    1500
tgcccgggtg aaaaaatac tcccaggcct cagctcgcgc ctcctcacga tcgcttttcg     1560
tataaaaacc atcctccttc gcgctccttt tcatccatat tctcactttt gtctctatcc    1620
cctcagctaa aaccaacacc tctaaatcat c                                   1651
```

<210> SEQ ID NO 12
<211> LENGTH: 1201
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
tgagtttctg ttttttcctt tttgcataac tgtcgacaag agacggtgta tgaagtgaag      60
aggaaacaca aggggtgcat ggacgttgag gaacagtaac attcgtgatg ggtctaggtg     120
attgggggca gtgtgccttc taatgcacac cagaaccaag ccattgagta tcgctatggc    180
ttgcctatga tagcatggac cgcagaaaga aaccttttg ctgctaactg ggaccagaat     240
agcgcggtct gtcatcaact aacgttatgg tcctctgtag cctgggaaga acggactgag    300
ggtgtttcgt tgaatgtcaa ggggcatgcg ccaaaaaaca catatgacgg gggaacatgc    360
ggaagcgcga ttgtgatttt cattctttt tcggtctgtg tgaacaattc atgcagcttc     420
acgagcatgt tcgatggaaa ggaacagtgc tctattttc agagtagtct agcataggat     480
ttgagagccg agttgcttgc ttacgatgtc actgtgtgga gtgttggagc gcaatccctg    540
ctttttcaat tatctttggc atacgtggaa gacctggccg ttcagtacac gcccgcgaaa    600
tgtcattcaa tgccctgtcc aatcttgacc ataggcttag acacggtccc ccaagcttcc    660
tccaaacaat cgcgtttatt tatatacttc atcatgcata tgagatcaca cctgttaaac    720
tagatcgcaa ccgtacaata gtgtgctctc agttgaccag gggcagctac aaaacggtcc    780
ggctggagtg ttttttttga cgtctaagcg tttacgtgcc attgactact tcgagctttc    840
aaacgcttgg cccagggagg tctcgacagc taagagaacg tacgcgacct tctctttggt    900
ccattgagca agtttccca cacacatagt agttggatat gcctgttcac catcgttggg    960
cattgcacca aaaggcatcc cgctgaaagc tgtcatgaaa ctcgttttga tggagttctc   1020
aatcacatca cctcacatca ttttgcaccc tgcccgggtg aaaaaatac tcccaggcct    1080 cagctcgcgc ctcctcacga tcgcttttcg tataaaaacc atcctccttc gcgctccttt   1140
tcatccatat tctcactttt gtctctatcc cctcagctaa aaccaacacc tctaaatcat   1200
c                                                                   1201
```

<210> SEQ ID NO 13
<211> LENGTH: 1609
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 13

| | | | | | |
|---|---|---|---|---|---|
| gactgtaaag | acggagggga | gcaccaggat | tagtaacgta | cactctctat | ctcaataaga | 60 |
| tttaatatga | attttctcag | aggacactgc | tcttcctacg | cgatgattca | actgctgccg | 120 |
| ttttctccca | tatccataca | gcgaggttta | gcaggtctat | ggtcgctctc | agacagcgat | 180 |
| tcgcgcccaa | aacagcattc | tcggcaatga | tttgaggctt | cgaaactgtt | cgcggaaata | 240 |
| ccacagaggt | gtgcattcac | tgatacatgt | acataggttg | atggtacaat | gacaagaaca | 300 |
| caggatagta | acatcgatcg | gaggcaactt | tggagctacc | ggatggccgg | gcatgagaaa | 360 |
| atctcgcatc | tgtaatacat | aaacgtctcc | gtatctttat | agggctcaat | tgcatttaca | 420 |
| ggtgaatatt | acaactaggc | actcttcttc | aaaagaaaca | ggatttggta | gtgattggtg | 480 |
| gactaatgga | cgaaagtgac | attctgttac | catgaagtcc | aaactgggga | tctcgtttga | 540 |
| ccggcattcg | cacctggtga | atctaggatg | cttggatgca | ggagccgccg | ctttccttgc | 600 |
| ttcctccttt | gagtgacatg | aattcagaag | tactgttttt | ctggagctca | ttctgcacat | 660 |
| ttgggggttg | ggtgcttaca | gtactgggga | tgacgttcac | ctacttgcct | ctctgttcaa | 720 |
| ttcacctcga | gagaaatgac | caaagtatct | gcgtctgagc | cagcgcctgg | atatatggcg | 780 |
| ttataaattc | ataaaagtgt | ctggagcgat | cctccagcag | gcgtgtttgt | ggactgcacg | 840 |
| caataccgcg | tcgccaaatt | cgccatcgac | gcgaaagagt | gcgattctcg | cgctcgaacg | 900 |
| caagttgtgc | ctgtgtggtg | taacgtttga | ggaaaatatc | ctgcatgaat | gggacatgcg | 960 |
| cactgaggag | ttcctctcac | tgggattgat | acagaagaag | gtgttactca | tcccctagga | 1020 |
| gctcgtttct | atgattaggc | aatttcgact | ccagcaccgg | tatgttcgta | ccaaagggcc | 1080 |
| atagctccaa | ggataaggaa | aaatagacct | cacctcatgc | tcagctgaac | aagttgtggt | 1140 |
| gaagtacgtg | cctcggggat | tcaaccatcc | atatccaatc | atttcataat | gcatggctgc | 1200 |
| atctctacac | actaagtggt | gtctactttg | gagggtacca | aaactttgtt | cccaatgcat | 1260 |
| tactttgtaa | atgctttgta | ataacgcga | gacgcgtcga | tattgtggag | ttgtgtgagg | 1320 |
| ggtgggaaca | aaattgtacc | gcaaccccac | cacaatgcgc | gcatgaatct | gctcaaccat | 1380 |
| gtccttgaca | gaagaggcag | gtccaatgga | tactccatcc | ccaccccgcg | ccctttcaa | 1440 |
| ccccgagtct | tctgtaattc | ctaatatagc | ctttcaaagc | gtgtcagggc | actgcattct | 1500 |
| ccttcaagca | tcagcttaca | ttgccggaag | tgttataaaa | aggcgcctcc | ctttgttttc | 1560 |
| tgatcctcat | cctcccccac | tttttctaaa | ccactaccca | ctatccaca | | 1609 |

<210> SEQ ID NO 14
<211> LENGTH: 1519
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

| | | | | | |
|---|---|---|---|---|---|
| ctggcaatag | ttagtgcacg | cttgtacgaa | tatgctgtgc | gctgtacaaa | ccaactttac | 60 |
| acacacgaga | tcaaaatctg | aatagtgacc | agactggcaa | aaagcaggtg | caattgccaa | 120 |
| aagttgacgc | tatatttaga | agtatgtcga | ttctctctat | ctgcggcttt | gcatatttcc | 180 |
| cgcctcctct | tcctttccca | ccttgtcccc | agtattcaac | tgaggccatt | actttgtata | 240 |

```
gtctagtaca tgtacaagtg aaattgagca tggaggcgaa ggccttggag caacagccgt    300
gcccacttct ttggtcctcc aattgcatgc aagcacggtg agggctgaca attaatgaat    360
gaaagattca atagtcgacg cgtttccagt ggacagtccc acagctctct caataccagt    420
ccccgaacgc cctcgcccat tccatcctcc ccccgccttg tgtccactgg atgctatgca    480
gatgggagca ctctgaggca tgattccaat cttttcaggc agttaccgtg cgcccactgt    540
ttattgctca cagtcgacaa cgtactccct acctccccat ctcatcccct cccacacttg    600
attagggcgc cacacagtgt atatataaaa atggtgagcg tggctgggtg tcgaagaaac    660
gtatgggagg atcttactaa aaaaaagcc gtccttggga caccgccccc attctctctg    720
cagtgactgc agcactgaac gcatcgagtg ctaccgaccc cgctccggac tttcacaaat    780
aggcatccta tcccgattct attttctgac catcctgccg acatgagttg gctgcagttt    840
gccccataat gtctgtgtgt ttaatgtcgc atgagaaaga atatgaaaga aagaaaaaag    900
agtgagaacg aaaggaaaaa gactgggatg taacgagtac aaagagaaac agccgctcat    960
gatacacaaa aatgaccccg tttggaaaat gaagtgggcg taacggttaa cattccgttg   1020 gcttttttcgt ttattggatt gcgaattgtt ggacccatga atgcatgcct cggaaaacaa   1080
atgggtgtcc attcgtacaa gtgttaagat aggttcaacc ttatcatcca acggtcgaca   1140
cgggaaatgg cagaccgcgc cttgaacgta acggccaaac gaaaaattag aaggcactat   1200
gttcatctat tgttcaatgc tgtgtctcaa agaagtccct cgctcattat tcagtccctc   1260
gccccaagta ccatagacga caagtgtcca aaaaaaaaa aaaaaaaaa aaacgcaatc   1320 taaaccaggt catggacacc gttacgctcg gtcaggggcc ttgccttagc ctctgtcgcg   1380
ttcgtataaa gcctgcggtt tcagcgaaac atttcccttt cttctttatc caattctcac   1440
cacttctttt cagaacccac ctataaacct acccacccca ctccaaccaa cccccacct   1500 tctcaaacaa acctccatc                                                1519
```

<210> SEQ ID NO 15
<211> LENGTH: 1000
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
cagttaccgt gcgcccactg tttattgctc acagtcgaca acgtactccc tacctcccca    60
tctcatcccc tcccacactt gattagggcg ccacacagtg tatatataaa aatggtgagc   120
gtggctgggt gtcgaagaaa cgtatgggag ggatcttact aaaaaaaagc cgtccttggg   180
acaccgcccc cattctctct gcagtgactg cagcactgaa cgcatcgagt gctaccgacc   240
ccgctccgga ctttcacaaa taggcatcct atcccgattc tattttctga ccatcctgcc   300
gacatgagtt ggctgcagtt tgccccataa tgtctgtgtg tttaatgtcg catgagaaag   360
aatatgaaag aaagaaaaaa gagtgagaac gaaaggaaaa agactgggat gtaacgagta   420
caaagagaaa cagccgctca tgatacacaa aaatgacccc gtttggaaaa tgaagtgggc   480
gtaacggtta acattccgtt ggcttttttcg tttattggat tgcgaattgt tggacccatg   540
aatgcatgcc tcggaaaaca aatgggtgtc cattcgtaca agtgttaaga taggttcaac   600
cttatcatcc aacggtcgac acgggaaatg gcagaccgcg ccttgaacgt aacggccaaa   660
cgaaaaatta gaaggcacta tgttcatcta ttgttcaatg ctgtgtctca agaagtccct   720
```

```
tcgctcatta ttcagtccct cgccccaagt accatagacg acaagtgtcc aaaaaaaaaa    780
aaaaaaaaaa aaaacgcaat ctaaaccagg tcatggacac cgttacgctc ggtcaggggc    840
cttgccttag cctctgtcgc gttcgtataa agcctgcggt ttcagcgaaa catttccctt    900
tcttctttat ccaattctca ccacttcttt tcagaaccca cctataaacc tacccacccc    960
actccaacca accccccacc ttctcaaaca aacctccatc                        1000

<210> SEQ ID NO 16
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ctttcacaaa taggcatcct atcccgattc tattttctga ccatcctgcc gacatgagtt     60
ggctgcagtt tgcccataa tgtctgtgtg tttaatgtcg catgagaaag aatatgaaag    120
aaagaaaaaa gagtgagaac gaaaggaaaa agactgggat gtaacgagta caaagagaaa    180
cagccgctca tgatacacaa aaatgacccc gtttggaaaa tgaagtgggc gtaacggtta    240
acattccgtt ggcttttcg tttattggat tgcgaattgt tggacccatg aatgcatgcc    300
tcggaaaaca aatgggtgtc cattcgtaca agtgttaaga taggttcaac cttatcatcc    360
aacggtcgac acgggaaatg gcagaccgcg ccttgaacgt aacggccaaa cgaaaaatta    420
gaaggcacta tgttcatcta tgttcaatg ctgtgtctca aagaagtccc tcgctcatta    480
ttcagtccct cgccccaagt accatagacg acaagtgtcc aaaaaaaaaa aaaaaaaaaa    540
aaaacgcaat ctaaaccagg tcatggacac cgttacgctc ggtcaggggc cttgccttag    600
cctctgtcgc gttcgtataa agcctgcggt ttcagcgaaa catttccctt tcttctttat    660
ccaattctca ccacttcttt tcagaaccca cctataaacc tacccacccc actccaacca    720
accccccacc ttctcaaaca aacctccatc                                    750

<210> SEQ ID NO 17
<211> LENGTH: 1000
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gagctcaaga tgaaggtgct caacgttgtc tatgtgacag atcgtcagga gcgtgtggag     60
gagtgcgtac tctgccggat gggcgtcaat gtcgaaggac tgcacgagca cccaccaagc    120
aggttctgag ctcaatattt ttttttcttt cttagacctc ttctttattg catcctatca    180
gccaacaaat tcccttcttt ttttactacc gcattccctt ttccttattg tgtgtttgtt    240
cttccatgcc tatcatcttg ggacgaacaa acagactatg gcataggga acggatatga    300 cagaaggcgc agttgaaaca gcatacaatc ctgggcaaac agtattttcc ggccttctta    360
ttctcctacc ttgctcgaat gagctcttgt atatagaata tccttttcag taaacaattt    420
cttaacctca tatgaatatt cgcagctgtg ccttcgctat gatcaggttg ccttgtcaag    480
gatcaagttg gcgtcgtcct tttgggttgg atcaggcagc atgccttgcc tgccaacgaa    540
agctggttgg cgagacaaga ggtagcaaca gcatttgcct ccgtatttcg aaaaatattt    600
```

| | |
|---|---|
| cacaaagaag aagggtgtgt cggctcaggc ccttacttcg cctgcgctca aaaacagac | 660 |
| agctgcggga tggatatcag cattttgaa tgaaaggggc agaagtggaa ggccgcatct | 720 |
| gtacgtcttc gccacggtag ttctactgga aaatcgcttg aagacgcatg agggatttag | 780 |
| aggctttaaa tccagccatg actgttttct tgaaacttct tttgcaaaga aaatagagct | 840 |
| gcagcgtgca ggcacaaaga gagtcggtgc tccctgctca cggaatatgc tggaaggttt | 900 |
| tctttgacga ggcggcacat atatatgggg cccgcgcctt cgttctttt cttctgtttc | 960 |
| ctcatcttct cttcactcct tcccgcaaac cacacacacc | 1000 |

<210> SEQ ID NO 18
<211> LENGTH: 800
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

| | |
|---|---|
| ttttactacc gcattcctt ttccttattg tgtgtttgtt cttccatgcc tatcatcttg | 60 |
| ggacgaacaa acagactatg gcataggga acggatatga cagaaggcgc agttgaaaca | 120 |
| gcatacaatc ctgggcaaac agtatttcc ggccttctta ttctcctacc ttgctcgaat | 180 |
| gagctcttgt atatagaata tccttttcag taaacaattt cttaacctca tatgaatatt | 240 |
| cgcagctgtg ccttcgctat gatcaggttg ccttgtcaag gatcaagttg cgtcgtcct | 300 |
| tttgggttgg atcaggcagc atgccttgcc tgccaacgaa agctggttgg cgagacaaga | 360 |
| ggtagcaaca gcatttgcct ccgtatttcg aaaaatattt cacaaagaag aagggtgtgt | 420 |
| cggctcaggc ccttacttcg cctgcgctca aaaacagac agctgcggga tggatatcag | 480 |
| cattttgaa tgaaaggggc agaagtggaa ggccgcatct gtacgtcttc gccacggtag | 540 |
| ttctactgga aaatcgcttg aagacgcatg agggatttag aggctttaaa tccagccatg | 600 |
| actgttttct tgaaacttct tttgcaaaga aaatagagct gcagcgtgca ggcacaaaga | 660 |
| gagtcggtgc tccctgctca cggaatatgc tggaaggttt tctttgacga ggcggcacat | 720 |
| atatatgggg cccgcgcctt cgttcttttt cttctgtttc ctcatcttct cttcactcct | 780 |
| tcccgcaaac cacacacacc | 800 |

<210> SEQ ID NO 19
<211> LENGTH: 599
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

| | |
|---|---|
| ccttttcagt aaacaatttc ttaacctcat atgaatattc gcagctgtgc cttcgctatg | 60 |
| atcaggttgc cttgtcaagg atcaagttgg cgtcgtcctt ttgggttgga tcaggcagca | 120 |
| tgccttgcct gccaacgaaa gctggttggc gagacaagag gtagcaacag catttgcctc | 180 |
| cgtatttcga aaaatatttc acaaagaaga agggtgtgtc ggctcaggcc cttacttcgc | 240 |
| ctgcgctcaa aaacagaca gctgcgggat ggatatcagc attttgaat gaaaggggca | 300 |
| gaagtggaag gccgcatctg tacgtcttcg ccacggtagt tctactggaa aatcgcttga | 360 |
| agacgcatga gggatttaga ggctttaaat ccagccatga ctgttttctt gaaacttctt | 420 |
| ttgcaaagaa aatagagctg cagcgtgcag gcacaaagag agtcggtgct ccctgctcac | 480 |

```
ggaatatgct ggaaggtttt ctttgacgag gcggcacata tatatggggc ccgcgccttc    540 gttcttttc ttctgtttcc tcatcttctc ttcactcctt cccgcaaacc acacacacc      599

<210> SEQ ID NO 20
<211> LENGTH: 400
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
cacaaagaag aagggtgtgt cggctcaggc ccttacttcg cctgcgctca aaaacagac     60 agctgcggga tggatatcag cattttttgaa tgaaaggggc agaagtggaa ggccgcatct   120
gtacgtcttc gccacggtag ttctactgga aaatcgcttg aagacgcatg agggatttag   180
aggctttaaa tccagccatg actgttttct tgaaacttct tttgcaaaga aaatagagct   240
gcagcgtgca ggcacaaaga gagtcggtgc tccctgctca cggaatatgc tggaaggttt   300
tctttgacga gcggcacat atatatgggg cccgcgcctt cgttctttt cttctgtttc    360 ctcatcttct cttcactcct tcccgcaaac acacacacc                          400

<210> SEQ ID NO 21
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
actgttttct tgaaacttct tttgcaaaga aaatagagct gcagcgtgca ggcacaaaga    60
gagtcggtgc tccctgctca cggaatatgc tggaaggttt ctttgacga ggcggcacat    120 atatatgggg cccgcgcctt cgttcttttt cttctgtttc ctcatcttct cttcactcct   180
tcccgcaaac acacacacc                                               200

<210> SEQ ID NO 22
<211> LENGTH: 999
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
aaagtgctgc ttcggaaccg ttagacaatg ttccgtgccc gacaagagca agtcttcttg    60
attgggaaaa ctttacaggg gagcagatcg aggctctcgg tgccgaagtg ctgatcctct   120
cagatttggt aaggaccatt tttcttcgtt tttttttgac ggcgtgtata tgtcagtcca   180
tgtttccagc cgtgctatgc ccacgcatta atcaaattgc cgtaaaagac ctatgatccg   240
acaaacatcg tgccacttgt tactgttctg aaggcaatgc ttgttaaagg cgtcaccgcg   300
tacatgtcct cagctattcg aaatccgcaa acatttatcg actttttttgc ccgtatcagt   360 aagtggttcc ccttgtgccg ttgcaccaac tgtgcttgac ccattgtatc gatttctgat   420
atagtatctt gaatgacgtt caaacagggc aagagtgcgt cggcgtagag gttcaggaaa   480
tagatctgag tagcactgag cacctgttct tctttgatga ggacagtg cagaccgtga     540 aggtgtttcg ccttttattat ccgtaaagaa tgataagcaa aaaaaaaaa aaataaacgc    600
```

```
gctatgcgaa cggttcattt tgcgatgtgt cttaaaaaca agttccaggc atggaaaaaa    660
cgatgattgg gtccggggcc gcggagcaca gcctcgcaga atcgtgaggg tgctggaggg    720
tgctggagca tggtggaacc tcgattagct catttccacg tacggctgta cgtgccagac    780
caaaactctt ttttgcattt ttttttctct ctggtgtgaa cgcattggcg agggcggagg    840
cacagagaag gcgatagaac gcggtggaac gaaaaggaac attgagcacg cagtggtgga    900
tcgcatctgc catataaaat acacgccccg ccttttgctt tccgttttcc tctttttttc    960
ttcactcatc cctccaacac tcacactcac atctacatc                           999

<210> SEQ ID NO 23
<211> LENGTH: 843
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
tgacggcgtg tatatgtcag tccatgtttc cagccgtgct atgcccacgc attaatcaaa     60
ttgccgtaaa agacctatga tccgacaaac atcgtgccac ttgttactgt tctgaaggca    120
atgcttgtta aaggcgtcac cgcgtacatg tcctcagcta ttcgaaatcc gcaaacattt    180
atcgactttt ttgcccgtat cagtaagtgg ttccccttgt gccgttgcac caactgtgct    240
tgacccattg tatcgatttc tgatatagta tcttgaatga cgttcaaaca gggcaagagt    300
gcgtcggcgt agaggttcag gaaatagatc tgagtagcac tgagcacctg ttcttctttg    360
atgaggagac agtgcagacc gtgaaggtgt ttcgcccttta ttatccgtaa agaatgataa    420
gcaaaaaaaa aaaaaaataa acgcgctatg cgaacggttc attttgcgat gtgtcttaaa    480
aacaagttcc aggcatggaa aaacgatga ttgggtccgg ggccgcggag cacagcctcg    540
cagaatcgtg agggtgctgg agggtgctgg agcatggtgg aacctcgatt agctcatttc    600
cacgtacggc tgtacgtgcc agaccaaaac tctttttgc attttttttt ctctctggtg    660
tgaacgcatt ggcgagggcg gaggcacaga gaaggcgata gaacgcggtg gaacgaaaag    720
gaacattgag cacgcagtgg tggatcgcat ctgccatata aaatacacgc cccgcctttt    780
gctttccgtt ttcctctttt tttcttcact catccctcca acactcacac tcacatctac    840
atc                                                                  843

<210> SEQ ID NO 24
<211> LENGTH: 599
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
ccattgtatc gatttctgat atagtatctt gaatgacgtt caaacagggc aagagtgcgt     60
cggcgtagag gttcaggaaa tagatctgag tagcactgag cacctgttct tctttgatga    120
ggagacagtg cagaccgtga aggtgtttcg ccttttattat ccgtaaagaa tgataagcaa    180
aaaaaaaaaa aaataaacgc gctatgcgaa cggttcattt tgcgatgtgt cttaaaaaca    240
agttccaggc atggaaaaaa cgatgattgg gtccggggcc gcggagcaca gcctcgcaga    300
atcgtgaggg tgctggaggg tgctggagca tggtggaacc tcgattagct catttccacg    360
```

| | |
|---|---|
| tacggctgta cgtgccagac caaaactctt ttttgcattt ttttttctct ctggtgtgaa | 420 |
| cgcattggcg agggcggagg cacagagaag gcgatagaac gcggtggaac gaaaaggaac | 480 |
| attgagcacg cagtggtgga tcgcatctgc catataaaat acacgccccg ccttttgctt | 540 |
| tccgttttcc tcttttttc ttcactcatc cctccaacac tcacactcac atctacatc | 599 |

<210> SEQ ID NO 25
<211> LENGTH: 399
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 25

| | |
|---|---|
| gctatgcgaa cggttcattt tgcgatgtgt cttaaaaaca agttccaggc atggaaaaaa | 60 |
| cgatgattgg gtccggggcc gcggagcaca gcctcgcaga atcgtgaggg tgctggaggg | 120 |
| tgctggagca tggtggaacc tcgattagct catttccacg tacggctgta cgtgccagac | 180 |
| caaaactctt ttttgcattt ttttttctct ctggtgtgaa cgcattggcg agggcggagg | 240 |
| cacagagaag gcgatagaac gcggtggaac gaaaaggaac attgagcacg cagtggtgga | 300 |
| tcgcatctgc catataaaat acacgccccg ccttttgctt tccgttttcc tcttttttc | 360 |
| ttcactcatc cctccaacac tcacactcac atctacatc | 399 |

<210> SEQ ID NO 26
<211> LENGTH: 199
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 26

| | |
|---|---|
| tttttctct ctggtgtgaa cgcattggcg agggcggagg cacagagaag gcgatagaac | 60 |
| gcggtggaac gaaaaggaac attgagcacg cagtggtgga tcgcatctgc catataaaat | 120 |
| acacgccccg ccttttgctt tccgttttcc tcttttttc ttcactcatc cctccaacac | 180 |
| tcacactcac atctacatc | 199 |

<210> SEQ ID NO 27
<211> LENGTH: 2331
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 27

| | |
|---|---|
| ggttccgaga ggtggatttg gtggaatgga tgcaaagtga ttcacaggaa acgattgtcg | 60 |
| gatccgattt caccttggcc aaatgatgag cggtcacatc gggcgccatt tcatttcata | 120 |
| ttgatatcca tcacagggaa acgcgcaaga tcgaacttaa ggcggtcgat gaggctggct | 180 |
| ggaagaggca ttgtccgtgt cggcgtagag agtacggaga ggaagagacg ctgtagtggt | 240 |
| ggatgttgtc gcgagctgga gagagccatg cggcggagct cactcggcgt gggatcaact | 300 |
| gtggggacgc agaataccag cgcaccgacc acgcagagtg atggtcatta ccaacaaaac | 360 |
| ataaacaaag gggcaaagga cctcactctt tgcatgcccc catcctccat cttcgcgctc | 420 |
| acatccgtcc ccctatttc gtgaaggcag gcactcattg taaagtggaa ggatgatgta | 480 |

-continued

| | |
|---|---|
| cgacgattgc ctgatatgag ctcagtatgc atcaagcaag ctagcttcgg acagacatca | 540 |
| acaaaagacc atactgaggc gggtcttgtg ccacttccaa caacatattt taccgacagc | 600 |
| gtggtacttt tagcttctgg gcgtaaagac aaacagaaag tatcgttcac ttccccaaac | 660 |
| cttctcatgc ctattgataa ttgttggttt agtgtctggc aaagcacaat ggaaaatgat | 720 |
| agttggcgaa actctatggc aagattacga gattacgctt atcgattggc gtcgagcgtg | 780 |
| tctctccgcc gtctatgacc tcgggcctag taaccaccgt gacagagatg gaatagttga | 840 |
| aggctatgga agcacccgtg agagaagatg gggttgtaca agaacggata aaccgaaaac | 900 |
| cataacgctg cgcgtgtggg gcaagtaatg cggatgatga cagcctgtgc ctgatgttca | 960 |
| cgttaaaaac ctcgtctctc tcacgcatca gggcgcgccc aaccacagaa acacgaagag | 1020 |
| gatcatgggg gatgagagac gagggcgagt gtgcaggaaa gcgtgtcgct agcatgacac | 1080 |
| aaagcagctg ctactagcct gcttagagcg caggccattg aacacaatac tgaactctag | 1140 |
| tccaggcggt ggtttcgagg agcagaaact agtatgctcg tgaagagggg cacgtcgggg | 1200 |
| gtggacggag ggaacaagtt gaggctatat aatgtcctct aaactcaccg tcgtcccgtc | 1260 |
| tttccttctc ttttctttct gtcttcttgc ctcttgcttt caatggtcct ccgcaacaat | 1320 |
| caacactaag ctccttacac cacttggtac agaccgctct ctcctctta cccactcgcc | 1380 |
| atctgctcac tacctcaaga tgcccatgct gacaccgtcc tcaagcccct tagcaggtat | 1440 |
| cgcaccctct tctccacttg atgctctatc tcacctattc atatgggca ctcccattct | 1500 |
| gtgtcgatac gatgcacatt ttttctttttt tcattttttg ccgccaattc tgtttgtgag | 1560 |
| tggccaggac tccgcgagat gtatattttt tttttcattc ttctaggggt agtcaatctc | 1620 |
| gctgggactg aattaaactg tgttttgtg caccctgagt taagcgttca tttctctgtt | 1680 |
| caccatatca tcatcccgca atgagctctc ggtctgcgcc catgcgtgtg ctgggatcgg | 1740 |
| ctccgcacag gcttccttc gcatactcat gcacagacac atgcacacat gcacacatgc | 1800 |
| tcagagtgac agtgcggata tatcgtggtg ctgtgcatgc cttgcgtgga ggcaggctgc | 1860 |
| tgtggtgtct cccggcctgg ggcattcgac gaggtgccga gtgccgaaga acaggaccta | 1920 |
| tccctgtgg cccccccgcct attttttttt tctttttttc attctttcat tcttttttgtt | 1980 |
| tttatatatc tgccccttca ctcttttatc ttttcactcg tccataccta acttcccgct | 2040 |
| gctccattcc aattacattc caactccatt ccaattacat tccaactcca ttccaacagc | 2100 |
| attcctagca ttctcattct ctccattcaa tctccttccc tctgacccga gctcacttt | 2160 |
| tgccacctgc tgcaccccctt cgcccaccac cctttgctc accgtgtgtt acctcccccg | 2220 |
| gtgctccttt ttttccattt ttgccgccct ttttcttatt tcttgctagg cccaccctct | 2280 |
| gtcactgcaa ttccgcccat tcacccgacc acctcgtcct ttcaggagcc a | 2331 |

<210> SEQ ID NO 28
<211> LENGTH: 2000
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

| | |
|---|---|
| cgcagagtga tggtcattac caacaaaaca taaacaaagg ggcaaaggac ctcactctttt | 60 |
| gcatgccccc atcctccatc ttcgcgctca catccgtccc cctatttttcg tgaaggcagg | 120 |
| cactcattgt aaagtggaag gatgatgtac gacgattgc tgatatgagc tcagtatgca | 180 |

```
tcaagcaagc tagcttcgga cagacatcaa caaaagacca tactgaggcg ggtcttgtgc    240
cacttccaac aacatatttt accgacagcg tggtactttt agcttctggg cgtaaagaca    300
aacagaaagt atcgttcact tccccaaacc ttctcatgcc tattgataat tgttggttta    360
gtgtctggca aagcacaatg gaaaatgata gttggcgaaa ctctatggca agattacgag    420
attacgctta tcgattggcg tcgagcgtgt ctctccgccg tctatgacct cgggcctagt    480
aaccaccgtg acagagatgg aatagttgaa ggctatggaa gcacccgtga gagaagatgg    540
ggttgtacaa gaacggataa accgaaaacc ataacgctgc gcgtgtgggg caagtaatgc    600
ggatgatgac agcctgtgcc tgatgttcac gttaaaaacc tcgtctctct cacgcatcag    660
ggcgcgccca accacagaaa cacgaagagg atcatggggg atgagagacg agggcgagtg    720
tgcaggaaag cgtgtcgcta gcatgacaca aagcagctgc tactagcctg cttagagcgc    780
aggccattga acacaatact gaactctagt ccaggcggtg gtttcgagga gcagaaacta    840
gtatgctcgt gaagaggggc acgtcggggg tggacggagg gaacaagttg aggctatata    900
atgtcctcta aactcaccgt cgtcccgtct ttccttctct tttctttctg tcttcttgcc    960
tcttgctttc aatggtcctc cgcaacaatc aacactaagc tccttacacc acttggtaca    1020
gaccgctcct ctcctcttac ccactcgcca tctgctcact acctcaagat gcccatgctg    1080
acaccgtcct caagccccct agcaggtatc gcaccctctt ctccacttga tgctctatct    1140
cacctattca tatggggcac tcccattctg tgtcgatacg atgcacattt tttctttttt    1200
cattttttgc cgccaattct gtttgtgagt ggccaggact ccgcgagatg tatatttttt    1260
ttttcattct tctaggggta gtcaatctcg ctgggactga attaaactgt gttttgtgc     1320 accctgagtt aagcgttcat ttctctgttc accatatcat catcccgcaa tgagctctcg    1380
gtctgcgccc atgcgtgtgc tgggatcggc tccgcacagg cttcctttcg catactcatg    1440
cacagacaca tgcacacatg cacacatgct cagagtgaca gtgcggatat atcgtggtgc    1500
tgtgcatgcc ttgcgtggag gcaggctgct gtggtgtctc ccggcctggg gcattcgacg    1560
aggtgccgag tgccgaagaa caggacctat ccctgtggc cccccgccta ttttttttt     1620 ctttttttca ttctttcatt cttttgtttt ttatatatct gccccttcac tctttatct     1680 tttcactcgt ccatacctca cttcccgctg ctccattcca attacattcc aactccattc    1740
caattacatt ccaactccat tccaacagca ttcctagcat tctcattctc tccattcaat    1800
ctccttccct ctgacccgag ctcactttt gccacctgct gcacccttc gcccaccacc      1860 cttttgctca ccgtgtgtta cctcccccgg tgctccttt tttccatttt tgccgccctt     1920
tttcttattt cttgctaggc ccaccctctg tcactgcaat tccgcccatt cacccgacca    1980
cctcgtcctt tcaggagcca                                                2000
```

```
<210> SEQ ID NO 29
<211> LENGTH: 1812
<212> TYPE: DNA
<213> ORGANISM: Escherichia coli
<220> FEATURE:
<221> NAME/KEY: CDS
<222> LOCATION: (1)..(1809)

<400> SEQUENCE: 29 atg tta cgt cct gta gaa acc cca acc cgt gaa atc aaa aaa ctc gac    48
Met Leu Arg Pro Val Glu Thr Pro Thr Arg Glu Ile Lys Lys Leu Asp
  1               5                  10                  15 ggc ctg tgg gca ttc agt ctg gat cgc gaa aac tgt gga att gat cag    96
Gly Leu Trp Ala Phe Ser Leu Asp Arg Glu Asn Cys Gly Ile Asp Gln
```

```
                  20                  25                  30
cgt tgg tgg gaa agc gcg tta caa gaa agc cgg gca att gct gtg cca       144
Arg Trp Trp Glu Ser Ala Leu Gln Glu Ser Arg Ala Ile Ala Val Pro
         35                  40                  45 ggc agt ttt aac gat cag ttc gcc gat gca gat att cgt aat tat gcg       192
Gly Ser Phe Asn Asp Gln Phe Ala Asp Ala Asp Ile Arg Asn Tyr Ala
 50                  55                  60 ggc aac gtc tgg tat cag cgc gaa gtc ttt ata ccg aaa ggt tgg gca       240
Gly Asn Val Trp Tyr Gln Arg Glu Val Phe Ile Pro Lys Gly Trp Ala
 65                  70                  75                  80 ggc cag cgt atc gtg ctg cgt ttc gat gcg gtc act cat tac ggc aaa       288
Gly Gln Arg Ile Val Leu Arg Phe Asp Ala Val Thr His Tyr Gly Lys
                 85                  90                  95 gtg tgg gtc aat aat cag gaa gtg atg gag cat cag ggc ggc tat acg       336
Val Trp Val Asn Asn Gln Glu Val Met Glu His Gln Gly Gly Tyr Thr
        100                 105                 110 cca ttt gaa gcc gat gtc acg ccg tat gtt att gcc ggg aaa agt gta       384
Pro Phe Glu Ala Asp Val Thr Pro Tyr Val Ile Ala Gly Lys Ser Val
    115                 120                 125 cgt atc acc gtt tgt gtg aac aac gaa ctg aac tgg cag act atc ccg       432
Arg Ile Thr Val Cys Val Asn Asn Glu Leu Asn Trp Gln Thr Ile Pro
130                 135                 140 ccg gga atg gtg att acc gac gaa aac ggc aag aaa aag cag tct tac       480
Pro Gly Met Val Ile Thr Asp Glu Asn Gly Lys Lys Lys Gln Ser Tyr
145                 150                 155                 160 ttc cat gat ttc ttt aac tat gcc gga atc cat cgc agc gta atg ctc       528
Phe His Asp Phe Phe Asn Tyr Ala Gly Ile His Arg Ser Val Met Leu
                165                 170                 175 tac acc acg ccg aac acc tgg gtg gac gat atc acc gtg gtg acg cat       576
Tyr Thr Thr Pro Asn Thr Trp Val Asp Asp Ile Thr Val Val Thr His
        180                 185                 190 gtc gcg caa gac tgt aac cac gcg tct gtt gac tgg cag gtg gtg gcc       624
Val Ala Gln Asp Cys Asn His Ala Ser Val Asp Trp Gln Val Val Ala
    195                 200                 205 aat ggt gat gtc agc gtt gaa ctg cgt gat gcg gat caa cag gtg gtt       672
Asn Gly Asp Val Ser Val Glu Leu Arg Asp Ala Asp Gln Gln Val Val
210                 215                 220 gca act gga caa ggc act agc ggg act ttg caa gtg gtg aat ccg cac       720
Ala Thr Gly Gln Gly Thr Ser Gly Thr Leu Gln Val Val Asn Pro His
225                 230                 235                 240 ctc tgg caa ccg ggt gaa ggt tat ctc tat gaa ctg tgc gtc aca gcc       768
Leu Trp Gln Pro Gly Glu Gly Tyr Leu Tyr Glu Leu Cys Val Thr Ala
                245                 250                 255 aaa agc cag aca gag tgt gat atc tac ccg ctt cgc gtc ggc atc cgg       816
Lys Ser Gln Thr Glu Cys Asp Ile Tyr Pro Leu Arg Val Gly Ile Arg
        260                 265                 270 tca gtg gca gtg aag ggc gaa cag ttc ctg att aac cac aaa ccg ttc       864
Ser Val Ala Val Lys Gly Glu Gln Phe Leu Ile Asn His Lys Pro Phe
    275                 280                 285 tac ttt act ggc ttt ggt cgt cat gaa gat gcg gac ttg cgt ggc aaa       912
Tyr Phe Thr Gly Phe Gly Arg His Glu Asp Ala Asp Leu Arg Gly Lys
290                 295                 300 gga ttc gat aac gtg ctg atg gtg cac gac cac gca tta atg gac tgg       960
Gly Phe Asp Asn Val Leu Met Val His Asp His Ala Leu Met Asp Trp
305                 310                 315                 320 att ggg gcc aac tcc tac cgt acc tcg cat tac cct tac gct gaa gag      1008
Ile Gly Ala Asn Ser Tyr Arg Thr Ser His Tyr Pro Tyr Ala Glu Glu
                325                 330                 335 atg ctc gac tgg gca gat gaa cat ggc atc gtg gtg att gat gaa act      1056
Met Leu Asp Trp Ala Asp Glu His Gly Ile Val Val Ile Asp Glu Thr
```

```
Met Leu Asp Trp Ala Asp Glu His Gly Ile Val Val Ile Asp Glu Thr
                340                 345                 350 gct gct gtc ggc ttt aac ctc tct tta ggc att ggt ttc gaa gcg ggc      1104
Ala Ala Val Gly Phe Asn Leu Ser Leu Gly Ile Gly Phe Glu Ala Gly
            355                 360                 365 aac aag ccg aaa gaa ctg tac agc gaa gag gca gtc aac ggg gaa act      1152
Asn Lys Pro Lys Glu Leu Tyr Ser Glu Glu Ala Val Asn Gly Glu Thr
370                 375                 380 cag caa gcg cac tta cag gcg att aaa gag ctg ata gcg cgt gac aaa      1200
Gln Gln Ala His Leu Gln Ala Ile Lys Glu Leu Ile Ala Arg Asp Lys
385                 390                 395                 400 aac cac cca agc gtg gtg atg tgg agt att gcc aac gaa ccg gat acc      1248
Asn His Pro Ser Val Val Met Trp Ser Ile Ala Asn Glu Pro Asp Thr
                405                 410                 415 cgt ccg caa ggt gca cgg gaa tat ttc gcg cca ctg gcg gaa gca acg      1296
Arg Pro Gln Gly Ala Arg Glu Tyr Phe Ala Pro Leu Ala Glu Ala Thr
            420                 425                 430 cgt aaa ctc gac ccg acg cgt ccg atc acc tgc gtc aat gta atg ttc      1344
Arg Lys Leu Asp Pro Thr Arg Pro Ile Thr Cys Val Asn Val Met Phe
        435                 440                 445 tgc gac gct cac acc gat acc atc agc gat ctc ttt gat gtg ctg tgc      1392
Cys Asp Ala His Thr Asp Thr Ile Ser Asp Leu Phe Asp Val Leu Cys
450                 455                 460 ctg aac cgt tat tac gga tgg tat gtc caa agc ggc gat ttg gaa acg      1440
Leu Asn Arg Tyr Tyr Gly Trp Tyr Val Gln Ser Gly Asp Leu Glu Thr
465                 470                 475                 480 gca gag aag gta ctg gaa aaa gaa ctt ctg gcc tgg cag gag aaa ctg      1488
Ala Glu Lys Val Leu Glu Lys Glu Leu Leu Ala Trp Gln Glu Lys Leu
                485                 490                 495 cat cag ccg att atc atc acc gaa tac ggc gtg gat acg tta gcc ggg      1536
His Gln Pro Ile Ile Ile Thr Glu Tyr Gly Val Asp Thr Leu Ala Gly
            500                 505                 510 ctg cac tca atg tac acc gac atg tgg agt gaa gag tat cag tgt gca      1584
Leu His Ser Met Tyr Thr Asp Met Trp Ser Glu Glu Tyr Gln Cys Ala
        515                 520                 525 tgg ctg gat atg tat cac cgc gtc ttt gat cgc gtc agc gcc gtc gtc      1632
Trp Leu Asp Met Tyr His Arg Val Phe Asp Arg Val Ser Ala Val Val
530                 535                 540 ggt gaa cag gta tgg aat ttc gcc gat ttt gcg acc tcg caa ggc ata      1680
Gly Glu Gln Val Trp Asn Phe Ala Asp Phe Ala Thr Ser Gln Gly Ile
545                 550                 555                 560 ttg cgc gtt ggc ggt aac aag aaa ggg atc ttc act cgc gac cgc aaa      1728
Leu Arg Val Gly Gly Asn Lys Lys Gly Ile Phe Thr Arg Asp Arg Lys
                565                 570                 575 ccg aag tcg gcg gct ttt ctg ctg caa aaa cgc tgg act ggc atg aac      1776
Pro Lys Ser Ala Ala Phe Leu Leu Gln Lys Arg Trp Thr Gly Met Asn
            580                 585                 590 ttc ggt gaa aaa ccg cag cag gga ggc aaa caa tga                      1812
Phe Gly Glu Lys Pro Gln Gln Gly Gly Lys Gln
        595                 600

<210> SEQ ID NO 30
<211> LENGTH: 603
<212> TYPE: PRT
<213> ORGANISM: Escherichia coli

<400> SEQUENCE: 30

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
```

-continued

```
                20                  25                  30
Arg Trp Trp Glu Ser Ala Leu Gln Glu Ser Arg Ala Ile Ala Val Pro
             35                  40                  45

Gly Ser Phe Asn Asp Gln Phe Ala Asp Ala Asp Ile Arg Asn Tyr Ala
 50                  55                  60

Gly Asn Val Trp Tyr Gln Arg Glu Val Phe Ile Pro Lys Gly Trp Ala
 65                  70                  75                  80

Gly Gln Arg Ile Val Leu Arg Phe Asp Ala Val Thr His Tyr Gly Lys
             85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
            115                 120                 125

Arg Ile Thr Val Cys Val Asn Asn Glu Leu Asn Trp Gln Thr Ile Pro
130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
            195                 200                 205

Asn Gly Asp Val Ser Val Glu Leu Arg Asp Ala Asp Gln Gln Val Val
            210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
            275                 280                 285

Tyr Phe Thr Gly Phe Gly Arg His Glu Asp Ala Asp Leu Arg Gly Lys
            290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
            355                 360                 365

Asn Lys Pro Lys Glu Leu Tyr Ser Glu Ala Val Asn Gly Glu Thr
            370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
            435                 440                 445
```

```
Cys Asp Ala His Thr Asp Thr Ile Ser Asp Leu Phe Asp Val Leu Cys
    450                 455                 460
Leu Asn Arg Tyr Tyr Gly Trp Tyr Val Gln Ser Gly Asp Leu Glu Thr
465                 470                 475                 480
Ala Glu Lys Val Leu Glu Lys Glu Leu Leu Ala Trp Gln Glu Lys Leu
                485                 490                 495
His Gln Pro Ile Ile Ile Thr Glu Tyr Gly Val Asp Thr Leu Ala Gly
            500                 505                 510
Leu His Ser Met Tyr Thr Asp Met Trp Ser Glu Glu Tyr Gln Cys Ala
        515                 520                 525
Trp Leu Asp Met Tyr His Arg Val Phe Asp Arg Val Ser Ala Val Val
530                 535                 540
Gly Glu Gln Val Trp Asn Phe Ala Asp Phe Ala Thr Ser Gln Gly Ile
545                 550                 555                 560
Leu Arg Val Gly Gly Asn Lys Lys Gly Ile Phe Thr Arg Asp Arg Lys
                565                 570                 575
Pro Lys Ser Ala Ala Phe Leu Leu Gln Lys Arg Trp Thr Gly Met Asn
            580                 585                 590
Phe Gly Glu Lys Pro Gln Gln Gly Gly Lys Gln
            595                 600
```

<210> SEQ ID NO 31
<211> LENGTH: 1812
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1809)

<400> SEQUENCE: 31

```
atg ctc cgc ccc gtc gag acc ccc acc cgc gag atc aag aag ctc gac        48
Met Leu Arg Pro Val Glu Thr Pro Thr Arg Glu Ile Lys Lys Leu Asp
1               5                   10                  15 ggc ctc tgg gcc ttc tcg ctc gac cgc gag aac tgc ggc atc gac cag        96
Gly Leu Trp Ala Phe Ser Leu Asp Arg Glu Asn Cys Gly Ile Asp Gln
            20                  25                  30 cgt tgg tgg gag tcg gcc ctc cag gag tcg cgc gct atc gcc gtc ccc       144
Arg Trp Trp Glu Ser Ala Leu Gln Glu Ser Arg Ala Ile Ala Val Pro
        35                  40                  45 ggc tcg ttc aac gac cag ttc gcc gac gcc gac atc cgc aac tac gcc       192
Gly Ser Phe Asn Asp Gln Phe Ala Asp Ala Asp Ile Arg Asn Tyr Ala
    50                  55                  60 ggc aac gtc tgg tac cag cgc gag gtc ttt atc ccc aag ggc tgg gcc       240
Gly Asn Val Trp Tyr Gln Arg Glu Val Phe Ile Pro Lys Gly Trp Ala
65                  70                  75                  80 ggt cag cgc atc gtc ctc cgc ttc gac gcc gtc acc cac tac ggc aag       288
Gly Gln Arg Ile Val Leu Arg Phe Asp Ala Val Thr His Tyr Gly Lys
                85                  90                  95 gtc tgg gtc aac aac cag gag gtc atg gag cac cag ggc ggc tac acc       336
Val Trp Val Asn Asn Gln Glu Val Met Glu His Gln Gly Gly Tyr Thr
            100                 105                 110 ccc ttc gag gcc gac gtc acc ccc tac gtt atc gcc ggc aag tcg gtc       384
Pro Phe Glu Ala Asp Val Thr Pro Tyr Val Ile Ala Gly Lys Ser Val
        115                 120                 125 cgc atc acc gtc tgc gtc aac aac gag ttg aac tgg cag acc atc ccc       432
Arg Ile Thr Val Cys Val Asn Asn Glu Leu Asn Trp Gln Thr Ile Pro
```

```
                130                 135                 140
cct ggc atg gtc atc acc gac gag aac ggc aag aag aag cag tcg tac        480
Pro Gly Met Val Ile Thr Asp Glu Asn Gly Lys Lys Lys Gln Ser Tyr
145                 150                 155                 160 ttc cac gac ttc ttc aac tac gct ggc atc cac cgc tcg gtc atg ctc        528
Phe His Asp Phe Phe Asn Tyr Ala Gly Ile His Arg Ser Val Met Leu
                165                 170                 175 tac acc acc ccc aac acc tgg gtc gac gac atc acc gtc gtc acc cac        576
Tyr Thr Thr Pro Asn Thr Trp Val Asp Asp Ile Thr Val Val Thr His
            180                 185                 190 gtc gcc cag gac tgc aac cac gcc tcg gtc gac tgg cag gtc gtc gcc        624
Val Ala Gln Asp Cys Asn His Ala Ser Val Asp Trp Gln Val Val Ala
        195                 200                 205 aac ggt gat gtt tcg gtc gag ttg cgc gac gct gac cag cag gtc gtt        672
Asn Gly Asp Val Ser Val Glu Leu Arg Asp Ala Asp Gln Gln Val Val
    210                 215                 220 gcc acc ggc cag ggc acc tcg ggc acc ctc cag gtc gtc aac ccc cac        720
Ala Thr Gly Gln Gly Thr Ser Gly Thr Leu Gln Val Val Asn Pro His
225                 230                 235                 240 ctc tgg cag ccc ggc gag ggc tac ctc tac gag ttg tgc gtc acc gcc        768
Leu Trp Gln Pro Gly Glu Gly Tyr Leu Tyr Glu Leu Cys Val Thr Ala
                245                 250                 255 aag tcg cag acc gag tgc gac atc tac ccc ctc cgc gtc ggc atc cgc        816
Lys Ser Gln Thr Glu Cys Asp Ile Tyr Pro Leu Arg Val Gly Ile Arg
            260                 265                 270 tcg gtc gcc gtc aag ggc gag cag ttc ctc atc aac cac aag ccc ttc        864
Ser Val Ala Val Lys Gly Glu Gln Phe Leu Ile Asn His Lys Pro Phe
        275                 280                 285 tac ttc acc ggc ttc ggc cgc cac gag gac gct gat ctc cgc ggc aag        912
Tyr Phe Thr Gly Phe Gly Arg His Glu Asp Ala Asp Leu Arg Gly Lys
    290                 295                 300 ggc ttc gac aac gtc ctc atg gtc cac gac cac gcc ctc atg gac tgg        960
Gly Phe Asp Asn Val Leu Met Val His Asp His Ala Leu Met Asp Trp
305                 310                 315                 320 atc ggc gcc aac tcg tac cgc acc tcg cac tac ccc tac gcc gag gag       1008
Ile Gly Ala Asn Ser Tyr Arg Thr Ser His Tyr Pro Tyr Ala Glu Glu
                325                 330                 335 atg ttg gac tgg gcc gac gag cac ggc atc gtc gtc atc gac gag acc       1056
Met Leu Asp Trp Ala Asp Glu His Gly Ile Val Val Ile Asp Glu Thr
            340                 345                 350 gcc gct gtc ggc ttc aac ctc tcg ctc ggc atc ggc ttc gag gcc ggc       1104
Ala Ala Val Gly Phe Asn Leu Ser Leu Gly Ile Gly Phe Glu Ala Gly
        355                 360                 365 aac aag ccc aag gag ttg tac tcg gag gag gcc gtc aac ggc gag acc       1152
Asn Lys Pro Lys Glu Leu Tyr Ser Glu Glu Ala Val Asn Gly Glu Thr
    370                 375                 380 cag cag gcc cat ctc cag gcc atc aag gag ttg atc gcc cgc gac aag       1200
Gln Gln Ala His Leu Gln Ala Ile Lys Glu Leu Ile Ala Arg Asp Lys
385                 390                 395                 400 aac cac ccc tcc gtc gtc atg tgg tcg atc gcc aac gag ccc gac acc       1248
Asn His Pro Ser Val Val Met Trp Ser Ile Ala Asn Glu Pro Asp Thr
                405                 410                 415 cgt ccc cag ggt gcc cgc gag tac ttc gcc cct ctc gcc gag gcc acc       1296
Arg Pro Gln Gly Ala Arg Glu Tyr Phe Ala Pro Leu Ala Glu Ala Thr
            420                 425                 430 cgc aag ttg gac ccc acc cgc ccc att acc tgc gtc aac gtc atg ttc       1344
Arg Lys Leu Asp Pro Thr Arg Pro Ile Thr Cys Val Asn Val Met Phe
        435                 440                 445 tgc gac gcc cac acc gac acc atc tcg gac ctc ttc gac gtc ctc tgc       1392
```

-continued

```
Cys Asp Ala His Thr Asp Thr Ile Ser Asp Leu Phe Asp Val Leu Cys
            450                 455                 460 ctc aac cgc tac tac ggc tgg tac gtc cag tcg ggc gac ctc gag act       1440
Leu Asn Arg Tyr Tyr Gly Trp Tyr Val Gln Ser Gly Asp Leu Glu Thr
465                 470                 475                 480 gcc gag aag gtc ctc gag aag gag ttg ctc gcc tgg cag gag aag ctc       1488
Ala Glu Lys Val Leu Glu Lys Glu Leu Leu Ala Trp Gln Glu Lys Leu
                    485                 490                 495 cac cag ccc atc atc atc acc gag tac ggc gtc gac acc ctc gcc ggc       1536
His Gln Pro Ile Ile Ile Thr Glu Tyr Gly Val Asp Thr Leu Ala Gly
                500                 505                 510 ctc cac tcg atg tac acc gac atg tgg tcg gag gag tac cag tgc gcc       1584
Leu His Ser Met Tyr Thr Asp Met Trp Ser Glu Glu Tyr Gln Cys Ala
            515                 520                 525 tgg ctc gac atg tac cac cgc gtc ttt gac cgt gtc tcg gcc gtc gtc       1632
Trp Leu Asp Met Tyr His Arg Val Phe Asp Arg Val Ser Ala Val Val
530                 535                 540 ggc gag cag gtc tgg aac ttc gcc gac ttc gcc acc tcg cag ggc atc       1680
Gly Glu Gln Val Trp Asn Phe Ala Asp Phe Ala Thr Ser Gln Gly Ile
545                 550                 555                 560 ttg cgc gtc ggc ggc aac aag aag ggc atc ttc acc cgc gac cgc aag       1728
Leu Arg Val Gly Gly Asn Lys Lys Gly Ile Phe Thr Arg Asp Arg Lys
                565                 570                 575 ccc aag tcg gcc gcc ttc ttg ctc caa aag cgc tgg acc ggc atg aac       1776
Pro Lys Ser Ala Ala Phe Leu Leu Gln Lys Arg Trp Thr Gly Met Asn
                580                 585                 590 ttc ggt gag aag ccc cag cag ggc ggc aag cag taa                       1812
Phe Gly Glu Lys Pro Gln Gln Gly Gly Lys Gln
            595                 600
```

<210> SEQ ID NO 32
<211> LENGTH: 603
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160
```

```
Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Ala Val Asn Gly Glu Thr
    370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
        435                 440                 445

Cys Asp Ala His Thr Asp Thr Ile Ser Asp Leu Phe Asp Val Leu Cys
    450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
    530                 535                 540

Gly Glu Gln Val Trp Asn Phe Ala Asp Phe Ala Thr Ser Gln Gly Ile
545                 550                 555                 560

Leu Arg Val Gly Gly Asn Lys Lys Gly Ile Phe Thr Arg Asp Arg Lys
                565                 570                 575
```

```
Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln
        595                 600
```

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aatatctaga tgaccgtgcg cttttttgaga c        31

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agcaactagt cgtatatttg ttgaaaggtg        30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
attttctaga cacctcaaaa acgtgccttg        30

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aataactagt ggcggatatg tgtatggag        29

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aacgtctaga cgtgttatct tgcgctgc        28

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 38
tcatactagt gatgatttag aggtgttgg                                          29

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aagctctaga gactgtaaag acggagggg                                          29

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agtaactagt tgtggatagt gggtagtgg                                          29

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aaagtctaga ctggcaatag ttagtgcacg                                         30

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atcaactagt gatggaggtt tgtttgagaa g                                       31

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atcatctaga gagctcaaga tgaaggtgct c                                       31

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 44 ataactagt ggtgtgtgtg gtttgcggg                                    29

<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ttagtctaga aaagtgctgc ttcggaacc                                   29

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
agatactagt gatgtagatg tgagtgtgag                                  30

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aatatctaga ggttccgaga ggtggatttg                                  30

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ataatctaga tggctcctga aaggacgag                                   29

<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agcatctaga aaaactattc aataatgggc g                                31

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
```
atttctagaa tggcgagacg caggggggtag        30

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aatatctaga gagtgggcac tgaactaaaa ag        32

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aatatctaga gacactgcat gacgcgaaat c        31

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
aagtctagat gtcaatcatc tttgctgctg        30

<210> SEQ ID NO 54
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tgcgtctaga attataatta taatgaggaa gtg        33

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ttatctagag gcgagtggcg gactgc        26

<210> SEQ ID NO 56
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ttgtctagac aattggcaag gctgggttg                                29

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aatatctaga gatcctggtc gaaaaagaca g                             31

<210> SEQ ID NO 58
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
aatgtctaga tgagtttctg ttttttcctt tttgc                         35

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
aatatctaga tgaacaattc atgcagcttc acg                           33

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aatatctaga cgtctaagcg tttacgtgcc                               30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aatatctaga ctcgttttga tggagttctc                               30

<210> SEQ ID NO 62
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
atttctagat gcatttacag gtgaatatta c                             31

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ttatctagac ataaaagtgt ctggagcg                                    28

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ttatctagaa ctaagtggtg tctactttgg                                  30

<210> SEQ ID NO 65
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aattctagag gatactccat ccccaccc                                    28

<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
aattctagac agttaccgtg cgcccactg                                   29

<210> SEQ ID NO 67
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
aattctagac tttcacaaat aggcatccta tc                               32

<210> SEQ ID NO 68
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
aattctagag gcttttttcgt ttattggatt g                               31

<210> SEQ ID NO 69
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
acgtctagat atccaattct caccacttc                                    29

<210> SEQ ID NO 70
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aattctagat tttactaccg cattcccttt tc                                32

<210> SEQ ID NO 71
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
acgtctagac cttttcagta aacaatttc                                    29

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
atttctagac acaaagaaga agggtgtgtc                                   30

<210> SEQ ID NO 73
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
acgtctagaa ctgttttctt gaaacttc                                     28

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
agtaactagt tgacggcgtg tatatgtcag                                   30

```
<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
aggtactagt ccattgtatc gatttctgat                                        30

<210> SEQ ID NO 76
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
agtaactagt gctatgcgaa cggttcattt tg                                     32

<210> SEQ ID NO 77
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
aggtactagt ttttttctct ctggtgtgaa cg                                     32

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
aattctagac gcagagtgat ggtcattacc                                        30

<210> SEQ ID NO 79
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
aattctagac tctatggcaa gattacgag                                         29

<210> SEQ ID NO 80
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
aattctagat gctcgtgaag aggggcac                                          28

<210> SEQ ID NO 81
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
acgtctagac attttttgcc gccaattctg                                         30

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
atttctagac ccccgcctat ttttttttc                                          30
```